US011203646B2

(12) United States Patent
Fischer et al.

(10) Patent No.: US 11,203,646 B2
(45) Date of Patent: Dec. 21, 2021

(54) ANTI-CD3 EPSILON ANTIBODIES AND METHODS OF USE THEREOF

(71) Applicant: NovImmune SA, Geneva (CH)

(72) Inventors: Nicolas Fischer, Geneva (CH); Giovanni Magistrelli, Cessy (FR); Franck Gueneau, Saint Julien en Genevois (FR); Ulla Ravn, Le Lignon (CH)

(73) Assignee: NovImmune SA, Geneva (CH)

( * ) Notice: Subject to any disclaimer, the term of this patent is extended or adjusted under 35 U.S.C. 154(b) by 86 days.

(21) Appl. No.: 16/353,916

(22) Filed: Mar. 14, 2019

(65) Prior Publication Data

US 2019/0284297 A1  Sep. 19, 2019

Related U.S. Application Data

(60) Provisional application No. 62/643,095, filed on Mar. 14, 2018.

(51) Int. Cl.
| | | |
|---|---|---|
| C07K 16/30 | (2006.01) | |
| A61P 35/00 | (2006.01) | |
| C07K 16/46 | (2006.01) | |
| C07K 16/28 | (2006.01) | |

(52) U.S. Cl.
CPC .......... *C07K 16/3076* (2013.01); *A61P 35/00* (2018.01); *C07K 16/2809* (2013.01); *C07K 16/464* (2013.01); *C07K 2317/24* (2013.01); *C07K 2317/33* (2013.01); *C07K 2317/54* (2013.01); *C07K 2317/55* (2013.01); *C07K 2317/565* (2013.01)

(58) Field of Classification Search
CPC ..................... C07K 16/2809; C07K 2317/565; A61P 35/00
See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,522,811 | A | 6/1985 | Eppstein et al. |
| 4,544,545 | A | 10/1985 | Ryan et al. |
| 4,676,980 | A | 6/1987 | Segal et al. |
| 4,816,567 | A | 3/1989 | Cabilly et al. |
| 5,013,556 | A | 5/1991 | Woodle et al. |
| 5,225,539 | A | 7/1993 | Winter |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,916,771 | A | 6/1999 | Hori et al. |
| 5,939,598 | A | 8/1999 | Kucherlapati et al. |
| 6,075,181 | A | 6/2000 | Kucherlapati et al. |
| 6,150,584 | A | 11/2000 | Kucherlapati et al. |
| 6,528,624 | B1 | 3/2003 | Idusogie et al. |

FOREIGN PATENT DOCUMENTS

| | | |
|---|---|---|
| EP | 2 438 878 A1 | 4/2012 |
| WO | WO 91/00360 A1 | 1/1991 |
| WO | WO 92/20373 A1 | 11/1992 |
| WO | WO 93/08829 A1 | 5/1993 |
| WO | WO 94/02602 A1 | 2/1994 |
| WO | WO 95/22618 A1 | 8/1995 |
| WO | WO 96/27011 A1 | 9/1996 |
| WO | WO 96/33735 A1 | 10/1996 |
| WO | WO 96/34096 A1 | 10/1996 |
| WO | WO 99/53049 A1 | 10/1999 |
| WO | WO 02/31140 A1 | 4/2002 |
| WO | WO 2010/135558 A1 | 11/2010 |
| WO | WO 2011/084255 A2 | 7/2011 |
| WO | WO 2011/121110 A1 | 10/2011 |
| WO | WO 2012/023053 A2 | 2/2012 |
| WO | WO 2012/064792 A2 | 5/2012 |
| WO | WO 2012/135558 A1 | 10/2012 |
| WO | WO 2013/088259 A2 | 6/2013 |
| WO | WO 2014/087248 A2 | 6/2014 |
| WO | WO 2015/063339 A1 | 5/2015 |
| WO | WO 2015/095392 A1 | 6/2015 |
| WO | WO 2015/181098 A1 | 12/2015 |
| WO | WO 2016/020444 A1 | 2/2016 |
| WO | WO 2016/036937 A1 | 3/2016 |
| WO | WO 2016/110576 A1 | 7/2016 |

(Continued)

OTHER PUBLICATIONS

Baldrick, P., "Pharmaceutical Excipient Development: The Need for Preclinical Guidance," Regulatory Toxicology and Pharmacology 32:210-218 (2000).

Baudino, L. et al., "Crucial Role of Aspartic Acid at Position 265 in the CH2 Domain for Murine IgG2a and IgG2b Fc-Associated Effector Functions," The Journal of Immunology, 181:6664-6669 (2008).

Bobo, R. H. et al., "Convection-enhanced delivery of macromolecules in the brain," Proc. Natl. Acad. Sci. USA, 91:2076-2080 (1994).

Bowie, J. U. et al., "A Method to Identify Protein Sequences That Fold into a Known Three-Dimensional Structure," Science, 253:164-170 (1991).

Brodeur, B. R. et al., "Mouse-Human Myeloma Partners for the Production of Heterohybridomas," Monoclonal Antibody Production Techniques and Applications, Marcel Dekker, Inc., New York, 1987, pp. 51-63.

(Continued)

*Primary Examiner* — Daniel E Kolker
*Assistant Examiner* — Brian Hartnett
(74) *Attorney, Agent, or Firm* — Cooley LLP; Cynthia A. Kozakiewicz; Ivor R. Elrifi

(57) ABSTRACT

The disclosure relates to monoclonal antibodies and antigen binding fragments, variants, multimeric versions, or bispecifics thereof that specifically bind CD3 epsilon (CD3ε), as well as methods of making and using these anti-CD3ε antibodies and antigen binding fragments thereof in a variety of therapeutic, diagnostic and prophylactic indications.

24 Claims, 5 Drawing Sheets
Specification includes a Sequence Listing.

(56) References Cited

FOREIGN PATENT DOCUMENTS

| | | | |
|---|---|---|---|
| WO | WO 2016/179518 A2 | 11/2016 | |
| WO | WO-2017009442 A1 * | 1/2017 | .............. A61P 37/02 |

OTHER PUBLICATIONS

Chappell, S. A. et al., "A 9-nt segment of a cellular mRNA can function as an internal ribosome entry site (IRES) and when present in linked multiple copies greatly enhances IRES activity," PNAS, 97(4):1536-1541 (2000).

Charman, W. N., "Lipids, Lipophilic Drugs, and Oral Drug Delivery—Some Emerging Concepts," Journal of Pharmaceutical Sciences, 89(8):967-978 (2000).

Chothia, C. & Lesk, A. M., "Canonical Structures for the Hypervariable Regions of Immunoglobulins," J. Mol. Biol., 196:901-917 (1987).

Chothia, C. et al., "Conformations of immunoglobulin hypervariable regions," Nature, 342:877-883 (1989).

Cole, S. P. C. et al., "The EBV-Hybridoma Technique and Its Application to Human Lung Cancer," Monoclonal Antibodies and Cancer Therapy, Alan R. Liss, Inc., 1985, pp. 77-96.

Cote, R. J. et al., "Generation of human monoclonal antibodies reactive with cellular antigens," Proc. Natl. Acad. Sci. USA, 80:2026-2030 (1983).

Davidson, B. L. et al., "A model system for in vivo gene transfer into the central nervous system using an adenoviral vector," Nature Genetics, 3:219-223 (1993).

Davies, D. R. & Padlan, E. A., "Antibody-Antigen Complexes," Annu. Rev. Biochem., 59:439-473 (1990).

Davis, J. H. et al., "SEEDbodies: fusion proteins based on strand-exchange engineered domain (SEED) $C_H3$ heterodimers in an Fc analogue platform for asymmetric binders or immunofusions and bispecific antibodies," Protein Engineering, Design & Selection, 23(4):195-202 (2010).

Eppstein, D. A. et al., "Biological activity of liposome-encapsulated murine interferon γ is mediated by a cell membrane receptor," Proc. Natl. Acad. Sci. USA, 82:3688-3692 (1985).

Fishwild, D. M. et al., "High-avidity human IgGK monoclonal antibodies from a novel strain of minilocus transgenic mice," Nature Biotechnology, 14:845-851 (1996).

Geller, A. I. & Freese, A., Infection of cultured central nervous system neurons with a defective herpes simplex virus 1 vector results in stable expression of *Escherichia coli* fi-galactosidase, Proc. Natl. Acad. Sci. USA, 87:1149-1153 (1990).

Geller, A. I. et al., "Long-term increases in neurotransmitter release from neuronal cells expressing a constitutively active adenylate cyclase from a herpes simplex virus type 1 vector," Proc. Natl. Acad. Sci. USA, 90:7603-7607 (1993).

Geller, A. I. et al., "An HSV-1 Vector Expressing Tyrosine Hydroxylase Causes Production and Release of L-DOPA from Cultured Rat Striatal Cells," Journal of Neurochemistry, 64(2):487-496 (1995).

Goding, J. W., "Production of Monoclonal Antibodies," ACPress, 1986, pp. 59-103.

Gramer, M. J. et al., "Production of stable bispecific IgG1 by controlled Fab-arm exchange—Scalability from bench to large-scale manufacturing by application of standard approaches," mAbs, 5(6):962-973 (2013); doi:10.4161/mabs.26233.

Gruber, M. et al., "Efficient tumor cell lysis mediated by a bispecific single chain antibody expressed in *Escherichia coli*," J Immunol, 152:5368-5374 (1994).

Gunasekaran, K. et al., "Enhancing Antibody Fc Heterodimer Formation through Electrostatic Steering Effects," The Journal of Biological Chemistry, 285(25):19637-19646 (2010).

Hellen, C. U. T. & Sarnow, P., "Internal ribosome entry sites in eukaryotic mRNA molecules," Genes & Development, 15:1593-1612 (2001).

Holliger, P. et al., ""Diabodies": Small bivalent and bispecific antibody fragments," Proc. Natl. Acad. Sci. USA, 90:6444-6448 (1993).

Hoogenboom, H. R. & Winter, G., "By-passing Immunisation—Human Antibodies from Synthetic Repertoires of Germline $V_H$ Gene Segments Rearranged in Vitro," J. Mol. Biol., 227:381-388 (1992).

Hwang, K. J. et al., "Hepatic uptake and degradation of unilamellar sphingomyelin/cholesterol liposomes: A kinetic study," Proc. Natl. Acad. Sci. USA, 77(7):4030-4034 (1980).

Jones, P. T. et al., "Replacing the complementarity determining regions in a human antibody with those from a mouse," Nature, 321:522-525 (1986).

Kaplitt, M. G. et al., "Long-term gene expression and phenotypic correction using adeno-associated virus vectors in the mammalian brain," Nature Genetics, 8:148-154 (1994).

Klein, C. et al., "Progress in overcoming the chain association issue in bispecific heterodimeric IgG antibodies," 4(6):653-663 (2012); doi:10.4161/mabs.21379.

Köhler, G. & Milstein, C., "Continuous cultures of fused cells secreting antibody of predefined specificity," Nature, 256:495-497 (1975).

Kontermann, R. E. et al., "Con1plen1ent recruitn1ent using bispecific diabodies," Nature Biotechnology, 15:629-631 (1997).

Kostelny, S. A. et al., "Formation of a bispecific antibody by the use of leucine zippers," The Journal of Immunology, 148(5): 1547-1553 (1992).

Kozbor, D. & Roder, J. C., "The production of monoclonal antibodies from human lymphocytes," Immunology Today, 4(3):72-79 (1983).

Kozbor, D. et al., "A human hybrid myeloma for production of human monoclonal antibodies," The Journal of Immunology, 133(6):3001-3005 (1984).

Le Gal La Salle, G. et al., "An Adenovirus Vector for Gene Transfer into Neurons and Glia in the Brain," Science, 259(5097):988-990 (1993).

Lonberg, N. et al., "Antigen-specific human antibodies from mice comprising four distinct genetic modifications," Nature, 368:856-859 (1994).

Lonberg, N. & Huszar, D., "Human Antibodies from Transgenic Mice," Intern. Rev. Immunol., 13:65-93 (1995).

Malmqvist, M., "Biospecific interaction analysis using biosensor technology," Nature, 361:186-187 (1993).

Marasco, W. A. et al., "Design, intracellular expression, and activity of a human anti-human immunodeficiency virus type 1 gp120 single-chain antibody," Proc. Natl. Acad. Sci. USA, 90:7889-7893 (1993).

Marks, J. D. et al., "By-passing Immunization: Human Antibodies from V-gene Libraries Displayed on Phage," J. Mol. Biol., 222:581-597 (1991).

Marks, J. D. et al., "By-passing immunization: building high affinity human antibodies by chain shuffling," Biotechnology, 10:779-783 (1992).

Martin, F. J. & Papahadjopoulos, D., "Irreversible Coupling of Immunoglobulin Fragments to Preformed Vesicles," The Journal of Biological Chemistry, 257(1):286-288 (1982).

Milstein, C. & Cuello, A. C., "Hybrid hybridomas and their use in immunohistochemistry," Nature, 305:537-540 (1983).

Moore, P. A. et al., "Application of dual affinity retargeting molecules to achieve optimal redirected T-cell killing of B-cell lymphoma," Blood, 117(17):4542-4551 (2011).

Morrison, P. F. et al., "High-flow microinfusion: tissue penetration and pharmacodynamics," Am J. Physiol., 266:R292-R305 (1994); www.physiology.org/journal/ajpregu.

Morrison, S. L., "Success in specification," Nature, 368:812-813 (1994).

Munson, P. J. & Rodbard, D., "Ligand: A Versatile Computerized Approach for Characterization of Ligand-Binding Systems," Analytical Biochemistry, 107:220-239 (1980).

Neuberger, M., "Generating high-avidity human Mabs in mice," Nature Biotechnology, 14:826 (1996).

(56) References Cited

OTHER PUBLICATIONS

Pessano, S. et al., "The T3/T cell receptor complex: antigenic distinction between the two 20-kd T3 (T3-δ and T3-ε) subunits," The EMBO Journal, 4(2):337-344 (1985).

Pörtner, L. M. et al., "T and NK cells of B cell NHL patients exert cytotoxicity against lymphoma cells following binding of bispecific tetravalent antibody CD19 X CD3 or CD19 X CD16," Cancer Immunol Immunother, 61:1869-1875 (2012).

Powell, M. F. et al., "Compendium of Excipients for Parenteral Formulations," PDA J Pharm Sci and Tech, 52:238-311 (1998).

Presta, L. G., "Antibody engineering," Current Opinion in Structural Biology, 2:593-596 (1992).

Ravn, U. et al., "By-passing in vitro screening—next generation sequencing technologies applied to antibody display and in silico candidate selection," Nucleic Acids Research, 38(21):e193, 11 pages (2009); doi:10.1093/nar/gkq789.

Ridgway, J. B. B. et al., "'Knobs-into-holes' engineering of antibody CH3 domains for heavy chain heterodimerization," Protein Engineering, 9(7):617-621 (1996).

Riechmann, L. et al., "Reshaping human antibodies for therapy," Nature, 332:323-327 (1988).

Strohl, W. R., "Optimization of Fc-mediated effector functions of monoclonal antibodies," Current Opinion in Biotechnology, 20:685-691 (2009).

Suresh, M. R. et al., "Bispecific Monoclonal Antibodies from Hybrid Hybridomas," Methods in Enzymology, 121:210-228 (1986).

Thornton, J. M. et al., "Prediction of progress at last," Nature, 354:105-106 (1991).

Traunecker, A. et al., "Bispecific single chain molecules (Janusins) target cytotoxic lymphocytes on HIV infected cells," The EMBO Journal, 10(12):3655-3659 (1991).

Tutt, A. et al., "Trispecific F(ab')₃ derivatives that use cooperative signaling via the TCR/CD3 complex and CD2 to activate and redirect resting cytotoxic T cells," The Journal of Immunology, 147:60-69 (1991).

Verhoeyen, M. et al., "Reshaping Human Antibodies: Grafting an Antilysozyme Activity," Science, 239:1534-1536 (1988).

Von Kreudenstein, T. S. et al., "Improving biophysical properties of a bispecific antibody scaffold to aid developability," mAbs, 5(5):646-654 (2013); doi:10-4161/mabs.25632.

Wang, W., "Lyophilization and development of solid protein pharmaceuticals," International Journal of Pharmaceutics, 203:1-60 (2000).

Wilkinson, D., "Ultimate Abs," The Scientist, 14(8):25-28 (2000).

Wolf, E. et al., "BiTEs: bispecific antibody constructs with unique anti-tumor activity," Drug Discov Today, 10(18):1237-1244 (2005).

Yang, Y. et al., "Cellular and Humoral Immune Responses to Viral Antigens Create Barriers to Lung-Directed Gene Therapy with Recombinant Adenoviruses," Journal of Virology, 69(4):2004-2015 (1995), with Figures, 9 pages.

* cited by examiner

SEQUENCE LISTING

```
<160> NUMBER OF SEQ ID NOS: 52

<210> SEQ ID NO 1
<211> LENGTH: 125
<212> TYPE: PRT
<213> ORGANISM: Artificial Sequence
<220> FEATURE:
<223> OTHER INFORMATION: mSP34VH amino acid sequence

<400> SEQUENCE: 1

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Leu
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 2
<211> LENGTH: 112
```

```
<212> TYPE: PRT
<213> ORGANISM: Artificial Sequence
<220> FEATURE:
<223> OTHER INFORMATION: mSP34VL amino acid sequence

<400> SEQUENCE: 2

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu Gly Gln Pro
            100                 105                 110

<210> SEQ ID NO 3
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 3

Gly Phe Thr Phe Asn Thr Tyr Ala
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 4

Ile Arg Ser Lys Tyr Asn Asn Tyr Ala Thr
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 5

Val Arg His Gly Asn Phe Gly Asn Ser Tyr Val Ser Trp Phe Ala Tyr
1               5                   10                  15

<210> SEQ ID NO 6
<211> LENGTH: 125
<212> TYPE: PRT
<213> ORGANISM: Artificial Sequence
<220> FEATURE:
<223> OTHER INFORMATION: huSP34_VH amino acid sequence

<400> SEQUENCE: 6

Glu Val Gln Leu Val Glu Ser Gly Gly Gly Leu Val Gln Pro Gly Gly
1               5                   10                  15
```

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
 50                  55                  60

Ser Val Lys Asp Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 7
<211> LENGTH: 9
<212> TYPE: PRT
<213> ORGANISM: Artificial Sequence
<220> FEATURE:
<223> OTHER INFORMATION: mSP34 CDRL3 amino acid sequence

<400> SEQUENCE: 7

Ala Leu Trp Tyr Ser Asn Leu Trp Val
1               5

<210> SEQ ID NO 8
<211> LENGTH: 9
<212> TYPE: PRT
<213> ORGANISM: Artificial Sequence
<220> FEATURE:
<223> OTHER INFORMATION: Fgta CDRL3 amino acid sequence
<220> FEATURE:
<221> NAME/KEY: misc_feature
<222> LOCATION: (3)..(5)
<223> OTHER INFORMATION: Xaa can be any naturally occurring amino acid

<400> SEQUENCE: 8

Ala Leu Xaa Xaa Xaa Asn Leu Trp Val
1               5

<210> SEQ ID NO 9
<211> LENGTH: 9
<212> TYPE: PRT
<213> ORGANISM: Artificial Sequence
<220> FEATURE:
<223> OTHER INFORMATION: Fgt b CDRL3 amino acid sequence
<220> FEATURE:
<221> NAME/KEY: misc_feature
<222> LOCATION: (5)..(7)
<223> OTHER INFORMATION: Xaa can be any naturally occurring amino acid

<400> SEQUENCE: 9

Ala Leu Trp Tyr Xaa Xaa Xaa Trp Val
1               5

<210> SEQ ID NO 10
<211> LENGTH: 9
<212> TYPE: PRT
<213> ORGANISM: Artificial Sequence
<220> FEATURE:
<223> OTHER INFORMATION: Fgt c CDRL3 amino acid sequence
<220> FEATURE:
<221> NAME/KEY: misc_feature
<222> LOCATION: (6)..(8)

```
<223> OTHER INFORMATION: Xaa can be any naturally occurring amino acid

<400> SEQUENCE: 10

Ala Leu Trp Tyr Ser Xaa Xaa Xaa Val
1               5

<210> SEQ ID NO 11
<211> LENGTH: 9
<212> TYPE: PRT
<213> ORGANISM: Artificial Sequence
<220> FEATURE:
<223> OTHER INFORMATION: Clone L3sp34-G1-1-R2-P1_B6 CDRL1 amino acid
      sequence

<400> SEQUENCE: 11

Thr Gly Ala Val Thr Thr Ser Asn Tyr
1               5

<210> SEQ ID NO 12
<211> LENGTH: 3
<212> TYPE: PRT
<213> ORGANISM: Artificial Sequence
<220> FEATURE:
<223> OTHER INFORMATION: Clone L3sp34-G1-1-R2-P1_B6  CDRL2 amino acid
      sequence

<400> SEQUENCE: 12

Gly Thr Asn
1

<210> SEQ ID NO 13
<211> LENGTH: 9
<212> TYPE: PRT
<213> ORGANISM: Artificial Sequence
<220> FEATURE:
<223> OTHER INFORMATION: Clone L3sp34-G1-1-R2-P1_B6 CDRL3 amino acid
      sequence

<400> SEQUENCE: 13

Ala Leu Trp Tyr Ala Asn Arg Trp Val
1               5

<210> SEQ ID NO 14
<211> LENGTH: 9
<212> TYPE: PRT
<213> ORGANISM: Artificial Sequence
<220> FEATURE:
<223> OTHER INFORMATION: Clone L3sp34-G1-2-R2-P1_A10 CDRL3 amino acid
      sequence

<400> SEQUENCE: 14

Ala Leu Trp Tyr Lys Gly Tyr Trp Val
1               5

<210> SEQ ID NO 15
<211> LENGTH: 9
<212> TYPE: PRT
<213> ORGANISM: Artificial Sequence
<220> FEATURE:
<223> OTHER INFORMATION: Clone L3sp34-G1-1-R2-P1_D8 CDRL3 amino acid
      sequence

<400> SEQUENCE: 15

Ala Leu Trp Tyr Asp Gly Thr Trp Val
1               5

<210> SEQ ID NO 16
```

```
<211> LENGTH: 9
<212> TYPE: PRT
<213> ORGANISM: Artificial Sequence
<220> FEATURE:
<223> OTHER INFORMATION: Clone L3sp34-G1-2-R2-P1_F8 - CDRL3 amino acid
      sequence

<400> SEQUENCE: 16

Ala Leu Trp Tyr Asp Gly Lys Trp Val
1               5

<210> SEQ ID NO 17
<211> LENGTH: 9
<212> TYPE: PRT
<213> ORGANISM: Artificial Sequence
<220> FEATURE:
<223> OTHER INFORMATION: Clone L3sp34-G1-1-R2-P1_A11 CDRL3 amino acid
      sequence

<400> SEQUENCE: 17

Ala Leu Trp Tyr Asp Gly Trp Trp Val
1               5

<210> SEQ ID NO 18
<211> LENGTH: 9
<212> TYPE: PRT
<213> ORGANISM: Artificial Sequence
<220> FEATURE:
<223> OTHER INFORMATION: Clone L3sp34-G1-2-R2-P1_A4 CDRL3 amino acid
      sequence

<400> SEQUENCE: 18

Ala Leu Trp Tyr Lys Gln Arg Trp Val
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 19

Ala Leu Trp Tyr Asn Gln His Trp Val
1               5

<210> SEQ ID NO 20
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 20
actggagctg tcaccactag caattat                                          27

<210> SEQ ID NO 21
<211> LENGTH: 9
<212> TYPE: DNA
<213> ORGANISM: Artificial Sequence
<220> FEATURE:
<223> OTHER INFORMATION: Synthetic Polynucleotide

<400> SEQUENCE: 21 ggtacaaac                                                               9

<210> SEQ ID NO 22
```

```
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 22
gcactgtggt atgccaaccg ctgggtg                                      27

<210> SEQ ID NO 23
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 23
gcactgtggt ataagggta ctgggtg                                       27

<210> SEQ ID NO 24
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 24
gcactgtggt atgacgggac ctgggtg                                      27

<210> SEQ ID NO 25
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 25
gcactgtggt atgacggcaa gtgggtg                                      27

<210> SEQ ID NO 26
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 26
gcactgtggt atgacggctg gtgggtg                                      27

<210> SEQ ID NO 27
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 27
gcactgtggt ataagcagag gtgggtg                                      27

<210> SEQ ID NO 28
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 28
```
gcactgtggt ataaccagca ctgggtg                                              27

<210> SEQ ID NO 29
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 29

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ala Asn
                85                  90                  95

Arg Trp Val Phe Gly Gly Gly Thr Lys Leu Thr Val Leu
            100                 105

<210> SEQ ID NO 30
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 30
cagactgtgg tgacccagga gccctcactg actgtgtccc caggagggac agtcactctg     60
acctgtcgct ccagcactgg agctgtcacc actagcaatt atgccaactg gttccagcag    120
aagcctggcc aagcccccg gggactgatt ggtggtacaa acaaaagagc ccccgggaca     180
cctgcccggt tctcaggctc cctgcttggg ggcaaagctg ccctgaccct ttcgggtgcg    240
cagcctgagg atgaggctga gtattactgc gcactgtggt atgccaaccg ctgggtgttc    300
ggcggaggga ccaagctgac cgtccta                                       327

<210> SEQ ID NO 31
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 31

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala

```
                65                  70                  75                  80
Gln Pro Glu Asp Glu Ala Glu Tyr Tyr Cys Ala Leu Trp Tyr Lys Gly
                        85                  90                  95

Tyr Trp Val Phe Gly Gly Gly Thr Lys Leu Thr Val Leu
            100                 105
```

<210> SEQ ID NO 32
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 32

```
cagactgtgg tgacccagga gccctcactg actgtgtccc caggagggac agtcactctg      60
acctgtcgct ccagcactgg agctgtcacc actagcaatt atgccaactg gttccagcag     120
aagcctggcc aagccccccg gggactgatt ggtggtacaa acaaaagagc cccggggaca     180
cctgcccggt tctcaggctc cctgcttggg ggcaaagctg ccctgaccct ttcgggtgcg     240
cagcctgagg atgaggctga gtattactgc gcactgtggt ataaggggta ctgggtgttc     300
ggcggaggga ccaagctgac cgtccta                                         327
```

<210> SEQ ID NO 33
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 33

```
Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
                20                  25                  30

Asn Tyr Ala Asn Trp Phe Gln Gln Lys Pro Gly Gln Ala Pro Arg Gly
            35                  40                  45

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Asp Gly
                85                  90                  95

Thr Trp Val Phe Gly Gly Gly Thr Lys Leu Thr Val Leu
            100                 105
```

<210> SEQ ID NO 34
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 34

```
cagactgtgg tgacccagga gccctcactg actgtgtccc caggagggac agtcactctg      60
acctgtcgct ccagcactgg agctgtcacc actagcaatt atgccaactg gttccagcag     120
aagcctggcc aagccccccg gggactgatt ggtggtacaa acaaaagagc cccggggaca     180
cctgcccggt tctcaggctc cctgcttggg ggcaaagctg ccctgaccct ttcgggtgcg     240
```
cagcctgagg atgaggctga gtattactgc gcactgtggt atgacgggac ctgggtgttc    300
ggcggaggga ccaagctgac cgtccta                                        327

<210> SEQ ID NO 35
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 35

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Asp Gly
                85                  90                  95

Lys Trp Val Phe Gly Gly Gly Thr Lys Leu Thr Val Leu
            100                 105

<210> SEQ ID NO 36
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 36
cagactgtgg tgacccagga gccctcactg actgtgtccc caggagggac agtcactctg    60
acctgtcgct ccagcactgg agctgtcacc actagcaatt atgccaactg gttccagcag    120
aagcctggcc aagcccccg gggactgatt ggtggtacaa acaaaagagc ccccgggaca    180 cctgcccgt tctcaggctc cctgcttggg ggcaaagctg ccctgaccct ttcgggtgcg    240
cagcctgagg atgaggctga gtattactgc gcactgtggt atgacggcaa gtgggtgttc    300
ggcggaggga ccaagctgac cgtccta                                        327

<210> SEQ ID NO 37
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 37

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

-continued

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Asp Gly
                 85                  90                  95

Trp Trp Val Phe Gly Gly Gly Thr Lys Leu Thr Val Leu
            100                 105

<210> SEQ ID NO 38
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 38
cagactgtgg tgacccagga gccctcactg actgtgtccc caggagggac agtcactctg      60
acctgtcgct ccagcactgg agctgtcacc actagcaatt atgccaactg gttccagcag     120
aagcctggcc aagccccccg gggactgatt ggtggtacaa acaaaagagc ccccgggaca     180
cctgcccggt tctcaggctc cctgcttggg ggcaaagctg ccctgaccct ttcgggtgcg     240
cagcctgagg atgaggctga gtattactgc gcactgtggt atgacggctg gtgggtgttc     300
ggcggaggga ccaagctgac cgtccta                                        327

<210> SEQ ID NO 39
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 39

Gln Thr Val Val Thr Gln Glu Pro Ser Leu Thr Val Ser Pro Gly Gly
 1                5                  10                  15

Thr Val Thr Leu Thr Cys Arg Ser Ser Thr Gly Ala Val Thr Thr Ser
                 20                  25                  30

Asn Tyr Ala Asn Trp Phe Gln Gln Lys Pro Gly Gln Ala Pro Arg Gly
             35                  40                  45

Leu Ile Gly Gly Thr Asn Lys Arg Ala Pro Gly Thr Pro Ala Arg Phe
     50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Lys Gln
                 85                  90                  95

Arg Trp Val Phe Gly Gly Gly Thr Lys Leu Thr Val Leu
            100                 105

<210> SEQ ID NO 40
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 40
cagactgtgg tgacccagga gccctcactg actgtgtccc caggagggac agtcactctg      60
acctgtcgct ccagcactgg agctgtcacc actagcaatt atgccaactg gttccagcag     120
aagcctggcc aagccccccg gggactgatt ggtggtacaa acaaaagagc ccccgggaca     180
cctgcccggt tctcaggctc cctgcttggg ggcaaagctg ccctgaccct ttcgggtgcg     240

```
cagcctgagg atgaggctga gtattactgc gcactgtggt ataagcagag gtgggtgttc    300
ggcggaggga ccaagctgac cgtccta                                        327
```

<210> SEQ ID NO 41
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 41

```
Gln Thr Val Val Thr Gln Glu Pro Ser Leu Thr Val Ser Pro Gly Gly
 1               5                  10                  15

Thr Val Thr Leu Thr Cys Arg Ser Ser Thr Gly Ala Val Thr Thr Ser
            20                  25                  30

Asn Tyr Ala Asn Trp Phe Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Asn Gln
                85                  90                  95

His Trp Val Phe Gly Gly Gly Thr Lys Leu Thr Val Leu
            100                 105
```

<210> SEQ ID NO 42
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 42

```
cagactgtgg tgacccagga gccctcactg actgtgtccc caggagggac agtcactctg    60
acctgtcgct ccagcactgg agctgtcacc actagcaatt atgccaactg gttccagcag    120
aagcctggcc aagccccccg gggactgatt ggtggtacaa acaaaagagc ccccgggaca    180
cctgcccggt tctcaggctc cctgcttggg ggcaaagctg ccctgaccct ttcgggtgcg    240
cagcctgagg atgaggctga gtattactgc gcactgtggt ataaccagca ctgggtgttc    300
ggcggaggga ccaagctgac cgtccta                                        327
```

<210> SEQ ID NO 43
<211> LENGTH: 375
<212> TYPE: DNA
<213> ORGANISM: Artificial Sequence
<220> FEATURE:
<223> OTHER INFORMATION: mSP34VH - polynucleotide sequence

<400> SEQUENCE: 43

```
gaagtgcagc tggtggaatc tggcggcgga ctggtgcagc ctaagggcag cctgaagctg    60
agctgtgccg ccagcggctt caccttcaac acctacgcca tgaactgggt cgcccaggcc    120
cctggcaaag gcctggaatg ggtggcccgg atcagaagca gtacaacaa ttacgccacc    180 tactacgccg acagcgtgaa ggaccggttc accatcagcc gggacgacag ccagagcctg    240
ctgtacctgc agatgaacaa cctgaaaacc gaggacaccg ccatgtacta ctgcgtgcgg    300
cacggcaact tcggcaacag ctatgtgtct tggtttgcct actggggcca gggcaccctc    360
```

```
gtgacagtct cgagc                                              375
```

<210> SEQ ID NO 44
<211> LENGTH: 327
<212> TYPE: DNA
<213> ORGANISM: Artificial Sequence
<220> FEATURE:
<223> OTHER INFORMATION: mSP34VL synthetic polynucleotide

<400> SEQUENCE: 44

```
caggccgtcg tgacacagga aagcgccctg acaaccagcc ctggcgagac agtgaccctg      60
acctgcagat ctagcacagg cgccgtgacc accagcaact acgccaactg ggtgcaggaa     120
aagcccgacc acctgttcac cggcctgatc ggcggcacca caaaagggc tccaggcgtg      180 ccagccagat tcagcggcag cctgattggc gataaggccg ccctgaccat cactggcgcc     240
cagacagagg acgaggccat ctacttttgc gccctgtggt acagcaacct gtgggtgttc     300
ggcggaggca ccaagctgac agtccta                                         327
```

<210> SEQ ID NO 45
<211> LENGTH: 98
<212> TYPE: PRT
<213> ORGANISM: Artificial Sequence
<220> FEATURE:
<223> OTHER INFORMATION: hIGHV3-73 framework

<400> SEQUENCE: 45

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys

<210> SEQ ID NO 46
<211> LENGTH: 294
<212> TYPE: DNA
<213> ORGANISM: Artificial Sequence
<220> FEATURE:
<223> OTHER INFORMATION: hIGHV3-73 Framework - polynucleotide sequence

<400> SEQUENCE: 46

```
gaggtgcagc tggtggagtc tgggggaggc ttggtccagc ctggggggtc cctgaaactc      60
tcctgtgcag cctctgggtt caccttcagt ggctctgcta tgcactgggt ccgccaggct     120
tccgggaaag gctggagtg gttggccgt attagaagca agctaacag ttacgcgaca        180 gcatatgctg cgtcggtgaa aggcaggttc accatctcca gagatgattc aaagaacacg     240
gcgtatctgc aaatgaacag cctgaaaacc gaggacacgg ccgtgtatta ctgt           294
```

<210> SEQ ID NO 47
<211> LENGTH: 24
<212> TYPE: DNA

<210> SEQ ID NO 47
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 47
gggttcacct tcaacaccta tgct                                          24

<210> SEQ ID NO 48
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 48
attagaagca aatataacaa ttacgcgaca                                    30

<210> SEQ ID NO 49
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 49
gtgagacacg ggaatttcgg caattcttat gtctcgtggt tcgcttac                48

<210> SEQ ID NO 50
<211> LENGTH: 375
<212> TYPE: DNA
<213> ORGANISM: Artificial Sequence
<220> FEATURE:
<223> OTHER INFORMATION: huSP34VH - polynucleotide sequence

<400> SEQUENCE: 50
gaggtgcagc tggtggagtc tgggggaggc ttggtccagc ctggggggtc cctgaaactc    60
tcctgtgcag cctctgggtt cacccttcaac acctatgcta tgaactgggt ccgccaggct  120
cccgggaaag gctggagtg ggttggccgt attagaagca aatataacaa ttacgcgaca    180
tactatgctg actcggtgaa agacaggttc accatctcca gagatgattc aaagaacacg   240
gcgtatctgc aaatgaacag cctgaaaacc gaggacacgg ccgtgtatta ctgtgtgaga   300
cacgggaatt tcggcaattc ttatgtctcg tggttcgctt actggggcca agggactctg   360
gtcacagtct cgagc                                                    375

<210> SEQ ID NO 51
<211> LENGTH: 90
<212> TYPE: PRT
<213> ORGANISM: Artificial Sequence
<220> FEATURE:
<223> OTHER INFORMATION: hIGLV7-46 Framework - polypeptide sequence

<400> SEQUENCE: 51

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Ala

```
<210> SEQ ID NO 52
<211> LENGTH: 270
<212> TYPE: DNA
<213> ORGANISM: Artificial Sequence
<220> FEATURE:
<223> OTHER INFORMATION: hIGLV7-46 Framework - polynucleotide sequence

<400> SEQUENCE: 52
caggctgtgg tgactcagga gccctcactg actgtgtccc caggagggac agtcactctc      60
acctgtggct ccagcactgg agctgtcacc agtggtcatt atccctactg gttccagcag     120
aagcctggcc aagcccccag gacactgatt tatgatacaa gcaacaaaca ctcctggaca     180
cctgcccggt tctcaggctc cctccttggg ggcaaagctg ccctgaccct ttcgggtgcg     240
cagcctgagg atgaggctga gtattactgc                                      270
```

Preceding amino acid fragment (positions 65–90):

Gln Pro Glu Asp Glu Ala Glu Tyr Tyr Cys

ANTI-CD3 EPSILON ANTIBODIES AND METHODS OF USE THEREOF

RELATED APPLICATIONS

The application claims the benefit of U.S. Provisional Application No. 62/643,095, filed Mar. 14, 2018, the contents of which are incorporated herein by reference in its entirety.

INCORPORATION-BY-REFERENCE OF SEQUENCE LISTING

The contents of the file named "NOVI-046_001US_SequenceListing_ST25.txt", which was created Mar. 14, 2019, and is 25.5 KB in size are hereby incorporated by reference in their entirety.

FIELD OF THE INVENTION

The disclosure relates to monoclonal antibodies and antigen binding fragments, variants, multimeric versions, or bispecifics thereof that specifically bind CD3 epsilon (CD3ε), as well as methods of making and using these anti-CD3ε antibodies and antigen binding fragments thereof in a variety of therapeutic, diagnostic and prophylactic indications.

BACKGROUND OF THE INVENTION

CD3 is a cell surface complex expressed on T cells in association with the T cell receptor. The CD3 complex is required for the activation of CD8+ and CD4+T lymphocytes. It is formed of three different but highly related chains: one CD3 gamma chain, one CD3 delta chain, and two CD3 epsilon chains, which associate with each other to form a CD3 epsilon/gamma heterodimer, and a CD3 epsilon/ delta heterodimer. The two CD3 heterodimers, together with the T cell receptor (TCR) and the signal-transducing zeta chain homodimer form the T cell receptor complex.

T cell retargeting (or T cell redirecting) bispecific antibodies (biAbs) is a novel class of therapeutics, capable of recruiting T cells to tumor cells and inducing tumor-specific (but WIC-independent) activation of T cell cytotoxicity. Typically, T cell retargeting biAbs contain a CD3 binding arm for T cell recruitment, and a tumor targeting arm specific for a tumor-associated antigen (TAA). Such a bispecific design enables the bringing of a T cell into a close contact with the target tumor cell, resulting in the formation of an immunological synapse, local T cell activation and the subsequent destruction of the target cell by perforin and granzyme released from T cell cytotoxic granules. In the last few years, T cell retargeting biAbs have shown considerable promise in clinical trials, leading to the regulatory approval of two molecules, catumaxomab (trade name Removab) for the treatment of malignant ascites and blinatumomab (Blincyto) for B-ALL (B-cell Acute Lymphoblastic Leukemia). As shown with Blincyto, biAb-mediated redirecting of T cell cytotoxic responses was able to induce a complete clearance of tumor cells from the bone marrow and a durable molecular remission in a significant proportion of B-ALL patients, thus demonstrating the power of this therapeutic approach.

Accordingly, there exists a need for fully human monoclonal antibodies and antigen-binding sequences thereof for use in T-cell retargeting.

SUMMARY OF THE INVENTION

The present invention provides antibodies or antigen binding fragments that bind CD3 epsilon (CD3ε). The CD3ε is human CD3ε or cynomolgus monkey CD3ε. The antibodies are monoclonal, bispecific or multimeric. The antibodies or antigen binding fragments is cynomolgus monkey, chimeric, humanized or fully human. The antibody or antigen binding fragment thereof is an IgG isotype such as IgG1 isotype.

The monoclonal antibody or antigen binding fragment thereof is for example, a single chain antibody (scAb), a Fab fragment, a F(ab')2 fragment, a single chain variable fragment (scFv), a scFv-Fc fragment, a multimeric antibody or a bispecific antibody.

In various aspects the invention provides monoclonal antibodies or antigen binding fragments have a variable heavy chain region comprising a complementarity determining region 1 (CDRH1) comprising the amino acid sequence of GFTFNTYA (SEQ ID NO: 3), a complementarity determining region 2 (CDRH2) comprising the amino acid sequence of IRSKYNNYAT (SEQ ID NO: 4) and a complementarity determining region 3 (CDRH3) comprising the amino acid sequence of VRHGNFGNSYVSWFAY (SEQ ID NO: 5); and a variable light chain region comprising a complementarity determining region 1 (CDRL1) comprising the amino acid sequence of TGAVTTSNY (SEQ ID NO: 11), a complementarity determining region 2 (CDRL2) comprising the amino acid sequence of GTN (SEQ ID NO: 12) and a complementarity determining region 3 (CDRL3) comprising the amino acid sequence selected from the group consisting of ALWYANRWV (SEQ ID NO: 13), ALWYKGYWV (SEQ ID NO: 14), ALWYDGTWV (SEQ ID NO: 15), ALWYDGKWV (SEQ ID NO: 16), ALWYDGWWV (SEQ ID NO: 17), ALWYKQRWV (SEQ ID NO: 18) and ALWYNQHWV (SEQ ID NO: 19).

In other aspects the invention provides a bispecific antibody having a first arm that binds CD3ε a comprising a variable heavy chain region comprising a complementarity determining region 1 (CDRH1) comprising the amino acid sequence of GFTFNTYA (SEQ ID NO: 3), a complementarity determining region 2 (CDRH2) comprising the amino acid sequence of IRSKYNNYAT (SEQ ID NO: 4) and a complementarity determining region 3 (CDRH3) comprising the amino acid sequence of VRHGNFGNSYVSWFAY (SEQ ID NO: 5); and a variable light chain region comprising a complementarity determining region 1 (CDRL1) comprising the amino acid sequence of TGAVTTSNY (SEQ ID NO: 11), a complementarity determining region 2 (CDRL2) comprising the amino acid sequence of GTN (SEQ ID NO: 12) and a complementarity determining region 3 (CDRL3) comprising the amino acid sequence selected from the group consisting of ALWYANRWV (SEQ ID NO: 13), ALWYKGYWV (SEQ ID NO: 14), ALWYDGTWV (SEQ ID NO: 15), ALWYDGKWV (SEQ ID NO: 16), ALWYDGWWV (SEQ ID NO: 17), ALWYKQRWV (SEQ ID NO: 18) and ALWYNQHWV (SEQ ID NO: 19); and a second arm that does not bind CD3ε.

In some embodiments, the antibody or antigen binding fragment thereof has a variable heavy chain region comprising the amino acid sequence of SEQ ID NO: 6 and a variable light chain comprising the amino acid sequence of SEQ ID NO: 29, 31, 33, 35, 37, 39 or 41.

In some embodiments, the bispecific antibody has a variable heavy chain region comprising the amino acid sequence of SEQ ID NO: 6 and a variable light chain comprising the amino acid sequence of SEQ ID NO: 29, 31, 33, 35, 37, 39 or 41.

In some embodiments, the antibody or antigen binding fragment thereof has a heavy chain region comprising a hIGHV3-73 framework region. For example, the variable heavy chain region comprises the amino acid sequence of SEQ ID NO: 6.

In some embodiments, the antibody or antigen binding fragment thereof has a variable light chain region comprising a hIGLV7-46 framework region. For example, the variable light chain region comprises the amino acid sequence of SEQ ID NO: 29, 31, 33, 35, 37, 39 or 41.

In some embodiments, the second arm of the bispecific antibody binds a tumor-associated antigen.

In some embodiments, suitable TAA, by way of non-limiting example, include CD20, HER2, HER3, EGFR, IGF1R, c-Met, PDGFR1, CD40, CD40L, CD30, CS1, CD70, glypican, mesothelin, PSMA, PSCA, MUC1, CA125, CEA, FRA, EpCAM, DR5, HGFR1, and/or 5T4.

In some embodiments, the bispecific antibody includes two copies of a single heavy chain polypeptide and a first light chain and a second light chain, wherein the first and second light chains are different.

In some embodiments, the bispecific antibody includes at least a portion of the first light chain is of the Kappa type and at least a portion of the second light chain is of the Lambda type. In some embodiments, the first light chain includes at least a Kappa constant region. In some embodiments, the first light chain further includes a Kappa variable region. In some embodiments, the first light chain further includes a Lambda variable region. In some embodiments, the second light chain includes at least a Lambda constant region. In some embodiments, the second light chain further includes a Lambda variable region. In some embodiments, the second light chain further includes a Kappa variable region. In some embodiments, the first light chain includes a Kappa constant region and a Kappa variable region, and wherein the second light chain includes a Lambda constant region and a Lambda variable region.

Also included in the invention is a pharmaceutical composition comprising the antibody or antigen binding fragment or the bispecific antibody according to the invention.

Further provided by the invention is a method of alleviating a symptom or disease or a method of T-cell retargeting by administering to a subject in need thereof a pharmaceutical composition comprising antibody according to the invention. The disease is for example, cancer.

DETAILED DESCRIPTION

Figure 1:
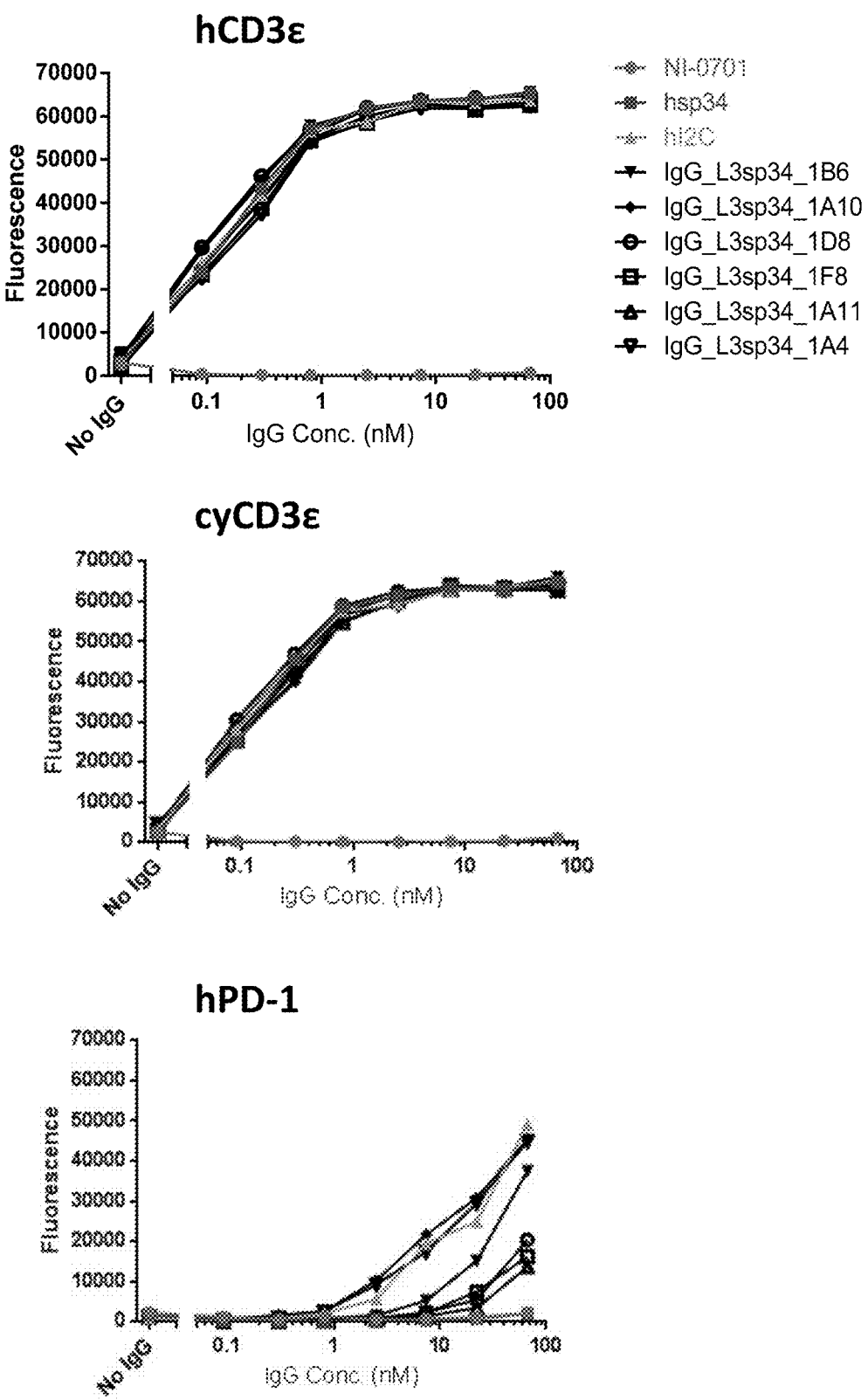
FIG. 1 Graphs showing the binding signals using ELISA and obtained with control and candidate anti-CD3ε antibodies against recombinant human CD3ε, cynomolgusCD3ε and human PD-1 recombinant proteins. NI-0701 is an anti human CCL5 mAb that was used as a negative control.
Figure 2:
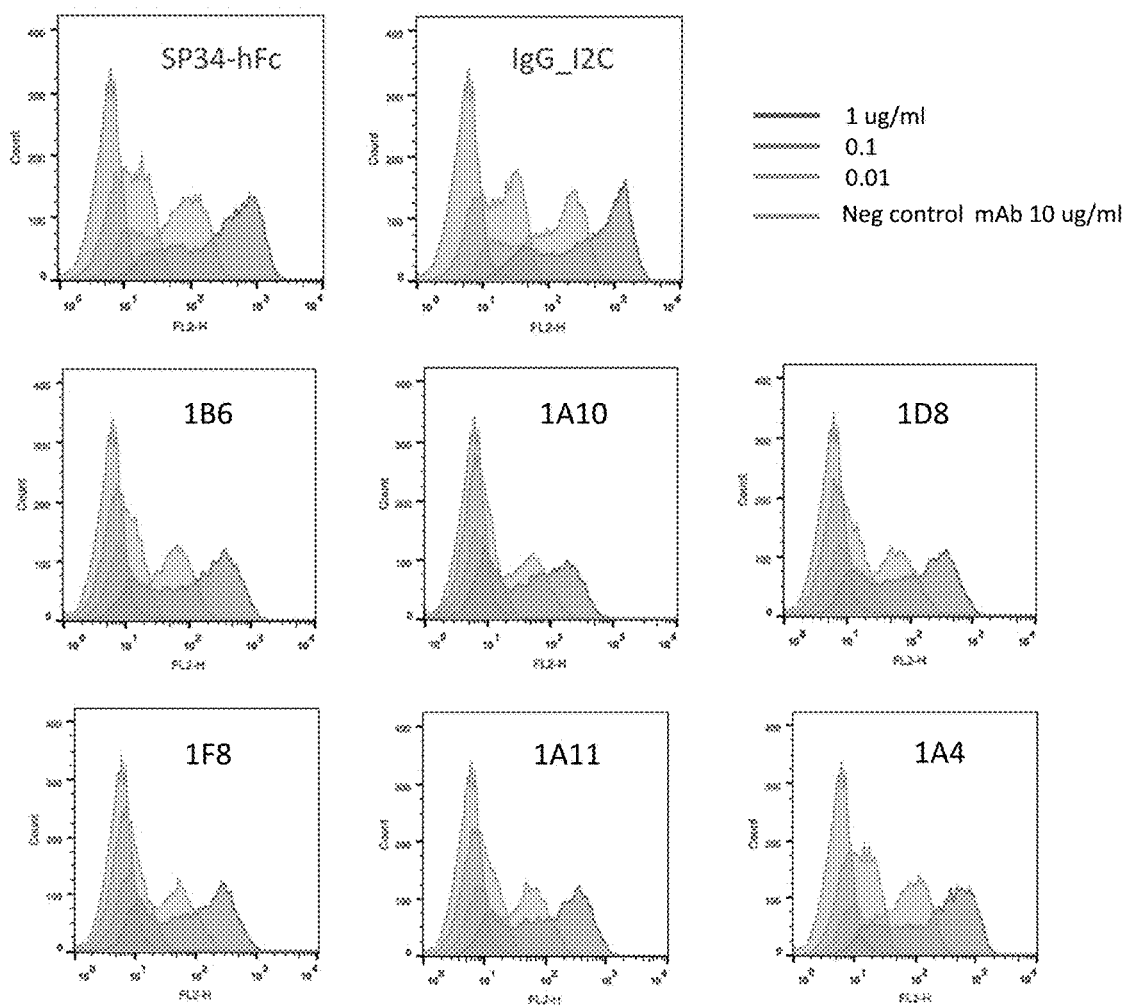
FIG. 2 Graphs showing the binding signals using FACS and obtained with control and candidate anti-CD3ε antibodies for staining of Jurkat T cells. NI-0701 was used as a negative control.

The present invention relates to the generation of a panel of antibodies that bind to human CD3 epsilon (CD3ε) and that are cross reactive with cynomolgus CD3ε. All these antibodies have a common VH chain and are therefore compatible with the generation of bispecific antibodies using the kappa lambda body technology (WO2014087248). The cross-reactivity with cynomolgus CD3ε is an important feature in order to facilitate preclinical development of T cell redirecting bispecific antibodies incorporating the anti-CD3ε antibodies described herein. Furthermore, these anti-CD3ε antibodies display different binding affinities. The affinity of the CD3 arm of a bispecific antibody can significantly modify the functional activity of the bispecific antibody and is it thus desirable to have anti-CD3ε antibodies with different affinities. The antibodies described herein can readily be exchanged for one another in the final bispecific kappa lambda construct as they all share the same heavy chain. In contrast to other T cell retargeting bispecific antibodies based on engineered molecules comprising either mutation or linker to achieve bispecificity, the kappa lambda bodies describes herein retain a native human IgG structure. This characteristic presents considerable advantages from a development perspective as these T cell retargeting agents share the drug-like properties of human monoclonal antibodies. It is anticipated that their unmodified human sequences and native structure, combined with favorable physicochemical properties, minimize the potential for immunogenicity when administered to patients.

The disclosure provides monoclonal antibodies that bind CD3ε. These antibodies are collectively referred to herein as anti-CD3ε monoclonal antibodies or anti-CD3ε mAbs. Preferably, the monoclonal antibodies are specific for at least human CD3ε. In some embodiments, the monoclonal antibodies that recognize human CD3ε are also cross-reactive for at least one other non-human CD3ε protein, such as, by way of non-limiting example, non-human primate CD3ε, e.g., cynomolgus monkey CD3ε, and/or rodent CD3ε.

The disclosure also provides monovalent antibodies and/or bispecific antibodies that include at least a first binding site that is specific for CD3ε. Preferably, the monovalent antibodies and/or bispecific antibodies are specific for at least human CD3ε. Exemplary embodiments, the monovalent antibodies and/or bispecific antibodies that recognize human CD3ε are also cross-reactive for at least one other non-human CD3ε protein, such as, by way of non-limiting example, non-human primate CD3ε, e.g., cynomolgus monkey CD3ε, and/or rodent CD3ε. The disclosure also provides antibodies that bind to the same epitope as an anti-CD3ε monovalent and/or an anti-CD3ε bispecific antibody disclosed herein.

In some embodiments, the bispecific antibody includes a first arm that binds CD3ε and a second arm that binds a second target that is not CD3ε. In some embodiments, the bispecific antibody includes a first arm that binds CD3ε and a second arm that binds a tumor associated antigen (TAA) including, by way of non-limiting example, EGFR, Her2, Her3, FOLR-1, MSLN, BSMA, CD20, CD19, CEA, PSMA, EpCAM, FSHR, CD123, CD38, CD33, gpA33, B7-H3, CDH3, SSTR2, TROP-2, GPC3, SLAMF7, ROR1 and/or 5T4. In some embodiments, the bispecific antibody includes a first arm that binds CD3ε and a second arm that binds a tumor associated antigen (TAA), where the first arm binds to CD3ε with low affinity, and the second arm binds to the TAA with high affinity. In some embodiments, the TAA is an antigen that is expressed on the cell surface of a cancer cell.

In some embodiments, the cancer cell is selected from a lung cancer cell, a bronchial cancer cell, a prostate cancer cell, a breast cancer cell, a colorectal cancer cell, a pancreatic cancer cell, an ovarian, a leukemia cancer cell, a lymphoma cancer cell, an esophageal cancer cell, a liver cancer cell, a urinary and/or bladder cancer cell, a renal cancer cell, an oral cavity cancer cell, a pharyngeal cancer cell, a uterine cancer cell, and/or a melanoma cancer cell. In some embodiments, suitable TAAs include, by way of non-limiting example, EGFR, Her2, Her3, FOLR-1, MSLN, BSMA, CD20, CD19, CEA, PSMA, EpCAM, FSHR, CD123, CD38, CD33, gpA33, B7-H3, CDH3, SSTR2, TROP-2, GPC3, SLAMF7, ROR1 and/or 5T4.

In some embodiments, the bispecific antibody is a fully human bispecific IgG format, such as the κλ-body format described in PCT Publication No. WO 2012/023053, the contents of which are incorporated by reference herein in their entirety.

Exemplary anti-CD3ε monoclonal antibodies of the disclosure and antigen binding fragments thereof include, for example, the 1B6 antibody, the 1A10 antibody, the 1D8 antibody, the 1F8 antibody, the 1A11 antibody and the 1A4 antibody or an antigen binding fragment thereof.

Exemplary anti-CD3ε bispecific antibodies of the disclosure in which at least one binding site is specific for CD3ε include, for example, 1B6 antibody, the 1A10 antibody, the 1D8 antibody, the 1F8 antibody, the 1A11 antibody and the 1A4 antibody or an antigen binding fragment thereof.

In some embodiments, exemplary anti-CD3ε monoclonal antibodies of the disclosure and antigen binding fragments thereof include heavy chain complementarity determining regions (CDRs) shown in Table 2 and light chain CDRs selected from the CDR sequences shown in Table 3, where the CDRs shown in Tables 2 and 3 are defined according to the IMGT nomenclature. (See, Examples)

In some embodiments, exemplary anti-CD3ε monoclonal antibodies of the disclosure and antigen binding fragments thereof include heavy chain complementarity determining regions (CDRs) shown in Table 2 and light chain CDRs selected from the CDR sequences shown in Table 3, where the CDRs shown in Tables 2 and 3 are defined according to the IMGT nomenclature. (See, Examples)

Anti-CD3ε Antibodies

Exemplary anti-CD3ε antibodies include the antibodies referred to herein as 1B6, 1A10, 1D8, 1F8, 1A11 or 1A4, or any fragments, variants, multimeric versions, or bispecifics thereof. These antibodies or any fragments, variants, multimeric versions, or bispecifics thereof are respectively referred to herein as "huCD3ε" antibodies. The huCD3ε antibodies of the disclosure include fully human monoclonal antibodies, as well as humanized monoclonal antibodies and chimeric antibodies, or any fragments, variants, multimeric versions, or bispecifics thereof. These antibodies show specificity for human CD3ε, and they have been shown to modulate, e.g., block, inhibit, reduce, antagonize, neutralize or otherwise interfere with at least one biological function or activity of CD3ε.

Biological function or activities of CD3ε include, by way of non-limiting example, T-cell receptor signaling. The antibodies are considered to completely modulate, block, inhibit, reduce, antagonize, neutralize or otherwise interfere with at least one functional activity of CD3ε when the level of functional activity of CD3ε in the presence of the antibody is decreased by at least 95%, e.g., by 96%, 97%, 98%, 99% or 100% as compared to the level of functional activity of CD3ε in the absence of binding with an antibody described herein. The antibodies are considered to partially modulate, block, inhibit, reduce, antagonize, neutralize or otherwise interfere with at least one functional activity of CD3ε when the level of functional activity of CD3ε in the presence of the antibody is decreased by less than 95%, e.g., 10%, 20%, 25%, 30%, 40%, 50%, 60%, 75%, 80%, 85% or 90% as compared to the level of functional activity of CD3ε in the absence of binding with an antibody described herein.

Each of the huCD3ε monoclonal antibodies or any fragments, variants, multimeric versions, or bispecifics thereof described herein includes a heavy chain variable region (VH) and a light chain variable region Each of the huCD3ε monoclonal antibodies or any fragments, variants, multimeric versions, or bispecifics thereof described herein includes a heavy chain variable region (VH) having a CDRH1 amino acid sequence of GFTFNTYA (SEQ ID NO:3) a CDRH2 amino acid sequence of IRSKYNNYAT (SEQ ID NO:4) and a CDRH3 amino acid sequence of VRHGNFGNSYVSWFAY (SEQ ID NO:5)

In some embodiments the heavy chain variable framework sequence is derived from hIGHV3-73.

An exemplary humanized heavy chain variable region includes the following amino acid sequence. CDRs as defined by IMGT nomenclature are underlined:

huSP34_VH
(SEQ ID NO: 6)
EVQLVESGGGLVQPGGSLKLSCAS<u>GFTFNTYA</u>MNWVRQAPGKGLEWVGR
<u>IRSKYNNYAT</u>YYADSVKDRFTISRDDSKNTAYLQMNSLKTEDTAVYYC<u>V</u>
<u>RHGNFGNSYVSWFAY</u>WGQGTLVTSS

A 1B6 huCD3ε monoclonal antibody or any fragments, variants, multimeric versions, or bispecifics thereof described herein includes a light chain variable region (VL) having a CDRL1 amino acid sequence of TGAVTTSNY (SEQ ID NO:11), a CDRL2 amino acid sequence of GTN (SEQ ID NO:12) and a CDRL3 amino acid sequence of ALWYANRWV (SEQ ID NO:13)

A 1A10 huCD3ε monoclonal antibody or any fragments, variants, multimeric versions, or bispecifics thereof described herein includes a light chain variable region (VL) having a CDRL1 amino acid sequence of TGAVTTSNY (SEQ ID NO:11), a CDRL2 amino acid sequence of GTN (SEQ ID NO:12) and a CDRL3 amino acid sequence of ALWYKGYWV (SEQ ID NO:14)

A 1D8 huCD3ε monoclonal antibody or any fragments, variants, multimeric versions, or bispecifics thereof described herein includes a light chain variable region (VL) having a CDRL1 amino acid sequence of TGAVTTSNY (SEQ ID NO:11), a CDRL2 amino acid sequence of GTN (SEQ ID NO:12) and a CDRL3 amino acid sequence of ALWYDGTWV (SEQ ID NO: 15)

A 1F8 huCD3ε monoclonal antibody or any fragments, variants, multimeric versions, or bispecifics thereof described herein includes a light chain variable region (VL) having a CDRL1 amino acid sequence of TGAVTTSNY (SEQ ID NO:11), a CDRL2 amino acid sequence of GTN (SEQ ID NO:12) and a CDRL3 amino acid sequence of ALWYDGKWV (SEQ ID NO:16)

A 1A11 huCD3ε monoclonal antibody or any fragments, variants, multimeric versions, or bispecifics thereof described herein includes a light chain variable region (VL) having a CDRL1 amino acid sequence of TGAVTTSNY (SEQ ID NO:11), a CDRL2 amino acid sequence of GTN (SEQ ID NO:12) and a CDRL3 amino acid sequence of ALWYDGWWV (SEQ ID NO:17)

A 1A4 huCD3ε monoclonal antibody or any fragments, variants, multimeric versions, or bispecifics thereof described herein includes a light chain variable region (VL) having a CDRL1 amino acid sequence of TGAVTTSNY (SEQ ID NO:11), a CDRL2 amino acid sequence of GTN (SEQ ID NO:12) and a CDRL3 amino acid sequence of ALWYKQRWV (SEQ ID NO:18)

A 1H4 huCD3ε monoclonal antibody or any fragments, variants, multimeric versions, or bispecifics thereof described herein includes a light chain variable region (VL) having a CDRL1 amino acid sequence of TGAVTTSNY (SEQ ID NO:11), a CDRL2 amino acid sequence of GTN (SEQ ID NO:12) and a CDRL3 amino acid sequence of ALWYNQHWV (SEQ ID NO:19)

In some embodiments, the anti-CD3ε antibody sequence or an antigen binding fragment thereof is used with a second antibody sequence or an antigen binding fragment thereof that binds a target other than CD3ε to produce a bispecific antibody referred to herein as an "anti-CD3ε bispecific antibody."

While antibody sequences below are provided herein as examples, it is to be understood that these sequences can be used to generate bispecific antibodies using any of a variety of art-recognized techniques. Examples of bispecific formats include but are not limited to fully human bispecific antibodies that include a common heavy chain, a kappa-type light chain, and a lambda-type light chain (PCT Publication No. WO 2012/023053), bispecific IgG based on Fab arm exchange (Gramer et al., 2013 MAbs. 5(6)); the CrossMab format (Klein C et al., 2012 MAbs 4(6)); multiple formats based on forced heterodimerization approaches such as SEED technology (Davis J H et al., 2010 Protein Eng Des Sel. 23(4):195-202), electrostatic steering (Gunasekaran K et al., J Biol Chem. 2010 285(25):19637-46.) or knob-into-hole (Ridgway J B et al., Protein Eng. 1996 9(7):617-21.) or other sets of mutations preventing homodimer formation (Von Kreudenstein T S et al., 2013 MAbs. 5(5):646-54.); fragment based bispecific formats such as tandem scFv (such as BiTEs) (Wolf E et al., 2005 Drug Discov. Today 10(18):1237-44.); bispecific tetravalent antibodies (Portner L M et al., 2012 Cancer Immunol Immunother. 61(10):1869-75.); dual affinity retargeting molecules (Moore P A et al., 2011 Blood. 117(17):4542-51), diabodies (Kontermann R E et al., Nat Biotechnol. 1997 15(7):629-31).

Definitions

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, or any fragments, variants, multimeric versions, or bispecifics thereof, including, e.g., polyclonal, monoclonal, chimeric, dAb (domain antibody), single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions" or "CDRs". The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is the to specifically bind an antigen when the dissociation constant is ≤1 µM; e.g., ≤100 nM, preferably ≤10 nM and more preferably ≤1 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is the to specifically bind to its target, when the equilibrium binding constant ($K_d$) is ≤1 µM, e.g., ≤100 nM, preferably ≤10 nM, and more preferably ≤1 nM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the disclosure include the nucleic acid molecules encoding the heavy chain immunoglobulin molecules, and nucleic acid molecules encoding the light chain immunoglobulin molecules described herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules, and the light chain immunoglobulin molecules described herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present disclosure, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibodies

Various procedures known within the art may be used for the production of polyclonal or monoclonal antibodies directed against a given target, such as, for example, CD3ε, a tumor associated antigen or other target, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

In some embodiments, the antibodies of the disclosure are monoclonal antibodies. Monoclonal antibodies are generated, for example, by using the procedures set forth in the Examples provided herein. Antibodies are also generated, e.g., by immunizing BALB/c mice with combinations of cell transfectants expressing high levels of a given target on their surface. Hybridomas resulting from myeloma/B cell fusions are then screened for reactivity to the selected target.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (MA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the disclosure can be readily isolated and sequenced using conventional procedures (e.g., by using oligonucleotide probes that are capable of binding specifically to genes encoding the heavy and light chains of murine antibodies). The hybridoma cells of the disclosure serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the disclosure, or can be substituted for the variable domains of one antigen-combining site of an antibody of the disclosure to create a chimeric bivalent antibody.

Monoclonal antibodies of the disclosure include humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization is performed, e.g., by following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539). In some instances, Fv framework residues of the human immunoglobulin are replaced by corresponding non-human residues. Humanized antibodies also comprise, e.g., residues which are found neither in the recipient antibody nor in the imported CDR or framework sequences. In general, the humanized antibody includes substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also includes at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Fully human antibodies are antibody molecules in which the entire sequence of both the light chain and the heavy chain, including the CDRs, arise from human genes. Such antibodies are termed "human antibodies", or "fully human antibodies" herein. Monoclonal antibodies can be prepared by using trioma technique; the human B-cell hybridoma technique (see Kozbor, et al., 1983 Immunol Today 4: 72); and the EBV hybridoma technique to produce monoclonal antibodies (see Cole, et al., 1985 In: MONOCLONAL ANTIBODIES AND CANCER THERAPY, Alan R. Liss, Inc., pp. 77-96). Monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. An example of such a nonhuman animal is a mouse termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds specifically to the relevant epitope with high affinity are disclosed in PCT publication WO 99/53049.

The antibody can be expressed by a vector containing a DNA segment encoding the single chain antibody described above.

These can include vectors, liposomes, naked DNA, adjuvant-assisted DNA. gene gun, catheters, etc. Vectors include chemical conjugates such as described in WO 93/64701, which has targeting moiety (e.g., a ligand to a cellular surface receptor), and a nucleic acid binding moiety (e.g., polylysine), viral vector (e.g., a DNA or RNA viral vector), fusion proteins such as described in PCT/US 95/02140 (WO 95/22618) which is a fusion protein containing a target moiety (e.g., an antibody specific for a target cell) and a nucleic acid binding moiety (e.g., a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g., infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g., adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

Bispecific antibodies are antibodies that have binding specificities for at least two different antigens. In the present case, one of the binding specificities is for a target such as CD3ε or any fragment thereof. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Bispecific and/or monovalent antibodies of the disclosure can be made using any of a variety of art-recognized techniques, including those disclosed in co-pending application WO 2012/023053, filed Aug. 16, 2011, the contents of which are hereby incorporated by reference in their entirety. The methods described in WO 2012/023053 generate bispecific antibodies that are identical in structure to a human immunoglobulin. This type of molecule is composed of two copies of a unique heavy chain polypeptide, a first light chain variable region fused to a constant Kappa domain and second light chain variable region fused to a constant Lambda domain. Each combining site displays a different antigen specificity to which both the heavy and light chain contribute. The light chain variable regions can be of the Lambda or Kappa family and are preferably fused to a Lambda and Kappa constant domains, respectively. This is preferred in order to avoid the generation of non-natural polypeptide junctions. However it is also possible to obtain bispecific antibodies of the disclosure by fusing a Kappa light chain variable domain to a constant Lambda domain for a first specificity and fusing a Lambda light chain variable domain to a constant Kappa domain for the second specificity. The bispecific antibodies described in WO 2012/023053 are referred to as IgGκλ antibodies or "κλ bodies," a new fully human bispecific IgG format. This κλ-body format allows the affinity purification of a bispecific antibody that is undistinguishable from a standard IgG molecule with characteristics that are undistinguishable from a standard monoclonal antibody and, therefore, favorable as compared to previous formats.

An essential step of the method is the identification of two antibody Fv regions (each composed by a variable light chain and variable heavy chain domain) having different antigen specificities that share the same heavy chain variable domain. Numerous methods have been described for the generation of monoclonal antibodies and fragments thereof. (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the sequence of both the light chain and the heavy chain, including the CDRs 1 and 2, arise from human genes. The CDR3 region can be of human origin or designed by synthetic means. Such antibodies are termed "human antibodies", or "fully human antibodies" herein. Human monoclonal antibodies can be prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: Monoclonal Antibodies and Cancer Therapy, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: Monoclonal Antibodies and Cancer Therapy, Alan R. Liss, Inc., pp. 77-96).

Monoclonal antibodies are generated, e.g., by immunizing an animal with a target antigen or an immunogenic fragment, derivative or variant thereof. Alternatively, the animal is immunized with cells transfected with a vector containing a nucleic acid molecule encoding the target antigen, such that the target antigen is expressed and associated with the surface of the transfected cells. A variety of techniques are well-known in the art for producing xenogenic non-human animals. For example, see U.S. Pat. Nos. 6,075,181 and 6,150,584, which is hereby incorporated by reference in its entirety.

Alternatively, the antibodies are obtained by screening a library that contains antibody or antigen binding domain sequences for binding to the target antigen. This library is prepared, e.g., in bacteriophage as protein or peptide fusions to a bacteriophage coat protein that is expressed on the surface of assembled phage particles and the encoding DNA sequences contained within the phage particles (i.e., "phage displayed library").

Hybridomas resulting from myeloma/B cell fusions are then screened for reactivity to the target antigen. Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

Although not strictly impossible, the serendipitous identification of different antibodies having the same heavy chain variable domain but directed against different antigens is highly unlikely. Indeed, in most cases the heavy chain contributes largely to the antigen binding surface and is also the most variable in sequence. In particular the CDR3 on the heavy chain is the most diverse CDR in sequence, length and structure. Thus, two antibodies specific for different antigens will almost invariably carry different heavy chain variable domains.

The methods disclosed in co-pending application WO 2012/023053 overcomes this limitation and greatly facilitates the isolation of antibodies having the same heavy chain variable domain by the use of antibody libraries in which the heavy chain variable domain is the same for all the library members and thus the diversity is confined to the light chain variable domain. Such libraries are described, for example, in co-pending applications WO 2010/135558 and WO 2011/084255, each of which is hereby incorporated by reference in its entirety. However, as the light chain variable domain is expressed in conjunction with the heavy variable domain, both domains can contribute to antigen binding. To further facilitate the process, antibody libraries containing the same heavy chain variable domain and either a diversity of Lambda variable light chains or Kappa variable light chains can be used in parallel for in vitro selection of antibodies against different antigens. This approach enables the identification of two antibodies having a common heavy chain but one carrying a Lambda light chain variable domain and the other a Kappa light chain variable domain that can be used as building blocks for the generation of a bispecific antibody in the full immunoglobulin format of the disclosure. The bispecific antibodies of the disclosure can be of different Isotypes and their Fc portion can be modified in order to alter the bind properties to different Fc receptors and in this way modify the effectors functions of the antibody as well as it pharmacokinetic properties. Numerous methods for the modification of the Fc portion have been described and are applicable to antibodies of the disclosure. (see for example Strohl, W R Curr Opin Biotechnol 2009 (6):685-91; U.S. Pat. No. 6,528,624; PCT/US2009/0191199 filed Jan. 9, 2009). The methods of the disclosure can also be used to generate bispecific antibodies and antibody mixtures in a F(ab')2 format that lacks the Fc portion.

The common heavy chain and two different light chains are co-expressed into a single cell to allow for the assembly of a bispecific antibody of the disclosure. If all the polypeptides get expressed at the same level and get assembled equally well to form an immunoglobulin molecule then the ratio of monospecific (same light chains) and bispecific (two different light chains) should be 50%. However, it is likely that different light chains are expressed at different levels and/or do not assemble with the same efficiency. Therefore, a means to modulate the relative expression of the different polypeptides is used to compensate for their intrinsic expression characteristics or different propensities to assemble with the common heavy chain. This modulation can be achieved via promoter strength, the use of internal ribosome entry sites (IRES) featuring different efficiencies or other types of regulatory elements that can act at transcriptional or translational levels as well as acting on mRNA stability. Different promoters of different strength could include CMV (Immediate-early Cytomegalovirus virus promoter); EF1-1α (Human elongation factor 1α-subunit promoter); Ubc (Human ubiquitin C promoter); SV40 (Simian virus 40 promoter). Different IRES have also been described from mammalian and viral origin. (See e.g., Hellen C U and Sarnow P. Genes Dev 2001 15: 1593-612). These IRES can greatly differ in their length and ribosome recruiting efficiency. Furthermore, it is possible to further tune the activity by introducing multiple copies of an IRES (Stephen et al. 2000 Proc Natl Acad Sci USA 97: 1536-1541). The modulation of the expression can also be achieved by multiple sequential transfections of cells to increase the copy number of individual genes expressing one or the other light chain and thus modify their relative expressions. The Examples provided herein demonstrate that controlling the relative expression of the different chains is critical for maximizing the assembly and overall yield of the bispecific antibody.

The co-expression of the heavy chain and two light chains generates a mixture of three different antibodies into the cell culture supernatant: two monospecific bivalent antibodies and one bispecific bivalent antibody. The latter has to be purified from the mixture to obtain the molecule of interest. The method described herein greatly facilitates this purification procedure by the use of affinity chromatography media that specifically interact with the Kappa or Lambda light chain constant domains such as the CaptureSelect Fab Kappa and CaptureSelect Fab Lambda affinity matrices (BAC BV, Holland). This multi-step affinity chromatography purification approach is efficient and generally applicable to antibodies of the disclosure. This is in sharp contrast to specific purification methods that have to be developed and optimized for each bispecific antibodies derived from quadromas or other cell lines expressing antibody mixtures. Indeed, if the biochemical characteristics of the different antibodies in the mixtures are similar, their separation using standard chromatography technique such as ion exchange chromatography can be challenging or not possible at all.

Other suitable purification methods include those disclosed in co-pending application PCT/IB2012/003028, filed on Oct. 19, 2012, published as WO2013/088259, the contents of which are hereby incorporated by reference in their entirety.

In other embodiments of producing bispecific antibodies, antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface includes at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the disclosure. Alternatively, an anti-antigenic arm of an immunoglobulin molecule can be combined with an arm which binds to a triggering molecule on a leukocyte such as a T-cell receptor molecule (e.g., CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present disclosure. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the disclosure with respect to effector function, so as to enhance, e.g., the effectiveness of the antibody in treating cancer and/or other diseases and disorders associated with aberrant CD3ε expression and/or activity. For example, silencing mutations can be introduced into the Fc region, thereby disrupting the binding of the Fc receptors and reducing antibody dependent cellular cytotoxicity (ADCC). Silencing mutations in the Fc region have been described in the art: for example the LALA and N297A mutations (Strohl, W., 2009, Curr. Opin. Biotechnol. vol. 20(6):685-691); and D265A (Baudino et al., 2008, J. Immunol. 181: 6664-69; Strohl, W., supra). Examples of silent Fc lgG1 antibodies comprise the so-called LALA mutant comprising L234A and L235A mutation in the lgG1 Fc amino acid sequence. Another example of a silent lgG1 antibody comprises the D265A mutation. Another silent lgG1 antibody comprises the N297A mutation, which results in aglycosylated/non-glycosylated antibodies. Glycosylation in the Fc region of the antibody may modulate binding to Fc receptors, and deglycosylation may lead to reduce binding. The antibody thus generated can have reduced internalization capability and/or decreased complement-mediated cell killing and ADCC.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al., J. Biol. Chem., 257: 286-288 (1982) via a disulfide-interchange reaction.

Use of Anti-CD3ε Antibodies

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the disclosure, which include an antibody of the disclosure, are used to treat or alleviate a symptom associated with a cancer, such as, by way of non-limiting example, leukemias, lymphomas, breast cancer, colon cancer, ovarian cancer, bladder cancer, prostate cancer, glioma, lung & bronchial cancer, colorectal cancer, pancreatic cancer, esophageal cancer, liver cancer, urinary bladder cancer, kidney and renal pelvis cancer, oral cavity & pharynx cancer, uterine corpus cancer, and/or melanoma The present disclosure also provides methods of treating or alleviating a symptom associated with a cancer. A therapeutic regimen is carried out by identifying a subject, e.g., a human patient suffering from (or at risk of developing) a cancer, using standard methods.

Efficaciousness of treatment is determined in association with any known method for diagnosing or treating the particular immune-related disorder. Alleviation of one or more symptoms of the immune-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

Antibodies directed against a target such as CD3ε, a tumor associated antigen or other antigen (or a fragment thereof) may be used in methods known within the art relating to the localization and/or quantitation of these targets, e.g., for use in measuring levels of these targets within appropriate physiological samples, for use in diagnostic methods, for use in imaging the protein, and the like). In a given embodiment, antibodies specific any of these targets, or derivative, fragment, analog or homolog thereof, that contain the antibody derived antigen binding domain, are utilized as pharmacologically active compounds (referred to hereinafter as "Therapeutics").

An antibody of the disclosure can be used to isolate a particular target using standard techniques, such as immunoaffinity, chromatography or immunoprecipitation. Antibodies of the disclosure (or a fragment thereof) can be used diagnostically to monitor protein levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and acquorin, and examples of suitable radioactive material include $^{125}I$, $^{131}I$, $^{35}S$ or $^{3}H$.

Antibodies of the disclosure, including polyclonal, monoclonal, humanized and fully human antibodies, may be used as therapeutic agents. Such agents will generally be employed to treat or prevent a disease or pathology associated with aberrant expression or activation of a given target in a subject. An antibody preparation, preferably one having high specificity and high affinity for its target antigen, is administered to the subject and will generally have an effect due to its binding with the target. Administration of the antibody may abrogate or inhibit or interfere with the signaling function of the target. Administration of the antibody may abrogate or inhibit or interfere with the binding of the target with an endogenous ligand to which it naturally binds.

A therapeutically effective amount of an antibody of the disclosure relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the disclosure may be, by way of nonlimiting example, from about 0.1 mg/kg body weight to about 50 mg/kg body weight. Common dosing frequencies may range, for example, from twice daily to once a week.

Antibodies or a fragment thereof of the disclosure can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

An antibody according to the disclosure can be used as an agent for detecting the presence of a given target (or a protein fragment thereof) in a sample. In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the disclosure can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies of the disclosure (also referred to herein as "active compounds"), and derivatives, fragments, analogs and homologs thereof, can be incorporated into pharmaceutical compositions suitable for administration. Such compositions typically comprise the antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL' (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The disclosure will be further described in the following examples, which do not limit the scope of the disclosure described in the claims.

EXAMPLES

Example 1. Protein Sequence Determination of the Anti-CD3 Mab SP34

The commercially available murine monoclonal antibody SP34 (Pessano et al. 1985, EMBO J; 4-2) binds specifically to both human and cynomolgous CD3ε. The amino acid sequences of the variable heavy and light chains of SP34 were determined de novo by Mass Spectrometry. Protein samples were solubilized in 8M urea, 50 mM triethylammonium bicarbonate (TEAB) buffer prior to reduction by addition of tris (2-carboxyethyl)phosphine (TCEP) to a final concentration of 5 mM and incubation at room temperature for 20 min. Subsequently iodoacetamide to a 10 mM final concentration was added and the sample was incubated at room temperature for another 20 mins in the dark. After alkylation the antibody sample was diluted 1:10 by addition of PNGase F enzyme buffer (New England Biolabs). To deglycosylate the sample 0.5 μl of PNGase was added for 25 μg of antibody. The sample was further incubated at 37° C. for 1 h. To separate the two species of antibody subunits (LC, HC) the alkylated and deglycosylated antibody sample was solubilized in sample loading buffer. Aliquots of 5 μg sample were loaded onto an SDS-PAGE gel. After the gel run (150 V, max. 400 mA, 75 min) the gel was incubated in 50% ethanol, 10% acetic acid for 30 min prior to gel staining with Coomassie Brilliant Blue (CBB G250). Gel slices from SDS-PAGE gels were prepared to enzymatic cleavage by 3 times swelling/shrinking in 100 mM ABC or 50 mM ABC, 60% ACN respectively. Each step was carried out for 30 min at room temperature. After the last shrinking step the gels slices were dried in open eppendorf cups for 15 min. Proteolysis was started by adding 3 volumes (with respect to approx. gel volume) of enzyme solutions with a enzyme/protein ratio of 1:50. Table 1 lists the enzyme solutions used for the proteolyses. Each proteolysis was carried out overnight. The resulting peptides were acidified with 0.5% (final) formic acid prior to mass spectrometry.

TABLE 1

List of proteolytic enzymes with their appropriate buffer solutions and incubations temperatures.

| | |
|---|---|
| Tr/TL/PK/ Elastase: | 50 mM ammonium bicarbonate, 10% acetonitrile (v/v) @ 37° C. |
| CT: | 100 mMTris-HCl, 10 mM CaCl2, 5% ACN (v/v), pH 8.0 @ 37° C. |
| LysC: | 50 mM Tris-HCl, 1 mM EDTA, 10% ACN (v/v), pH 8.5 @ 37° C. |
| GluC: | 50 mM Tris-HCl, 0.5 mMGlu-Glu, pH 8.0 @ 25° C. |
| LysN: | 100 mM Bis-Tris Propane, pH 10 @ 37° C. |
| AspN: | 50 mM Tris-HCl, 2.5 mM ZnSO4, pH 8.0 @ 37° C. |

The Agilent 1100 nanoLC system was coupled to an Orbitrap XL mass spectrometer (ThermoFisher, Bremen, Germany). Samples from proteolyses were applied to nanoLC-ESIMS/MS after acidification. After trapping and desalting the peptides on enrichment column (Zorbax SB C18, 0.3 mm×5 mm, Agilent) using 1% acetonitrile/0.5% formic acid solution for five minutes peptides were separated on Zorbax 300 SB C18, 75 µm×150 mm column (Agilent, Waldbronn) using an acetonitrile/0.1% formic acid gradient from 5% to 40% acetonitrile. MS overview spectra were automatically taken in FT-mode according to manufacturer's instrument settings for nanoLC-ESI-MSMS analyses, peptide fragmentation (CID and HCD) and detection operated in FT-mode too.

The iterative sequence assembly (data not shown) revealed one sequence candidate for the variable light chain and one candidate for the variable heavy chain of the monoclonal antibody.

The amino acid and nucleic acid sequences that were determined are listed below:

mSP34VH (SEQ ID NO: 1)
EVQLVESGGGLVQPKGSLKLSCAASGFTFNTYAMNWVRQAPGKGLEWVAR

IRSKYNNYATYYADSVKDRFTISRDDSQSLLYLQMNNLKTEDTAMYYCVR

HGNFGNSYVSWFAYWGQGTLVTVSS (SEQ ID NO: 43)
GAAGTGCAGCTGGTGGAATCTGGCGGCGGACTGGTGCAGCCTAAGGGCAG

CCTGAAGCTGAGCTGTGCCGCCAGCGGCTTCACCTTCAACACCTACGCCA

TGAACTGGGTGCGCCAGGCCCCTGGCAAAGGCCTGGAATGGGTGGCCCGG

ATCAGAAGCAAGTACAACAATTACGCCACCTACTACGCCGACAGCGTGAA

GGACCGGTTCACCATCAGCCGGGACGACAGCCAGAGCCTGCTGTACCTGC

AGATGAACAACCTGAAAACCGAGGACACCGCCATGTACTACTGCGTGCGG

CACGGCAACTTCGGCAACAGCTATGTGTCTTGGTTTGCCTACTGGGGCCA

GGGCACCCTCGTGACAGTCTCGAGC mSP341AVL (SEQ ID NO: 2)
QAVVTQESALTTSPGETVTLTCRSSTGAVTTSNYANWVQEKPDHLFTGLI

GGTNKRAPGVPARFSGSLIGDKAALTITGAQTEDEAIYFCALWYSNLWVF

GGGTKLTVLGQP (SEQ ID NO: 44)
CAGGCCGTCGTGACACAGGAAAGCGCCCTGACAACCAGCCCTGGCGAGAC

AGTGACCCTGACCTGCAGATCTAGCACAGGCGCCGTGACCACCAGCAACT

ACGCCAACTGGGTGCAGGAAAAGCCCGACCACCTGTTCACCGGCCTGATC

GGCGGCACCAACAAAAGGGCTCCAGGCGTGCCAGCCAGATTCAGCGGCAG

CCTGATTGGCGATAAGGCCGCCCTGACCATCACTGGCGCCCAGACAGAGG

ACGAGGCCATCTACTTTTGCGCCCTGTGGTACAGCAACCTGTGGGTGTTC

GGCGGAGGCACCAAGCTGACAGTCCTA

Example 2: Selection of Humanized Variants of Murine SP34

The amino acid sequence of the VH determined in Example 1 was used as a template for antibody humanization using the well described method of Complementarity Determining Region (CDR) grafting (Jones P et al, 1980, Nature) and using the hIGHV3-73 framework as an acceptor (IMGT nomenclature). The amino acid and nucleic acid sequences of the hIGHV3-73 framework are shown below. CDR sequences as defined by IMGT nomenclature are underlined.

hIGHV3-73 Framework (SEQ ID NO: 45)
EVQLVESGGGLVQPGGSLKLSCAAS<u>GFTFSGSA</u>MHWVRQASGKGLEWVGR <u>IRSKANSYAT</u>AYAASVKGRFTISRDDSKNTAYLQMNSLKTEDTAVYYC hIGHV3-73 Framework (SEQ ID NO: 46)
GAGGTGCAGCTGGTGGAGTCTGGGGGAGGCTTGGTCCAGCCTGGGGGGTC

CCTGAAACTCTCCTGTGCAGCCTCTGGGTTCACCTTCAGTGGCTCTGCTA

TGCACTGGGTCCGCCAGGCTTCCGGGAAAGGGCTGGAGTGGGTTGGCCGT

ATTAGAAGCAAAGCTAACAGTTACGCGACAGCATATGCTGCGTCGGTGAA

-continued
AGGCAGGTTCACCATCTCCAGAGATGATTCAAAGAACACGGCGTATCTGC

AAATGAACAGCCTGAAAACCGAGGACACGGCCGTGTATTACTGT

The amino acid and nucleic acid sequences of the CDRs of the humanized VH of SP34 are shown in the Table 2.

TABLE 2

CDR sequences of humanized SP34.

| | CDRH1 | CDRH2 | CDRH3 |
|---|---|---|---|
| Humanized SP34 | GFTFNTYA (SEQ ID NO: 3) GGGTTCACCTTCAAC ACCTATGCT (SEQ ID NO: 47) | IRSKYNNYAT (SEQ ID NO: 4) ATTAGAAGCAAATAT AACAATTACGCGACA (SEQ ID NO: 48) | VRHGNFGNSYVSWFAY (SEQ ID NO: 5) GTGAGACACGGGAATTTCGGCAATTCT TATGTCTCGTGGTTCGCTTAC (SEQ ID NO: 49) |

The amino acid and nucleic acid sequences of humanized SP34 variable heavy chain is shown below. CDR sequences as defined by IMGT nomenclature are underlined.

huSP34VH
(SEQ ID NO: 6)
EVQLVESGGGLVQPGGSLKLSCAAS<u>GFTFNTY</u>AMNWVRQAPGKGLEWVGR

<u>IRSKYNNYAT</u>YYADSVKDRFTISRDDSKNTAYLQMNSLKTEDTAVYYC<u>VR</u>

<u>HGNFGNSYVSWFAY</u>WGQGTLVTVSS huSP34VH
(SEQ ID NO: 50)
GAGGTGCAGCTGGTGGAGTCTGGGGGAGGCTTGGTCCAGCCTGGGGGGTC

CCTGAAACTCTCCTGTGCAGCCTCTGGGTTCACCTTCAACACCTATGCTA

TGAACTGGGTCCGCCAGGCTCCCGGGAAAGGGCTGGAGTGGGTTGGCCGT

ATTAGAAGCAAATATAACAATTACGCGACATACTATGCTGACTCGGTGAA

AGACAGGTTCACCATCTCCAGAGATGATTCAAAGAACACGGCGTATCTGC

AAATGAACAGCCTGAAAACCGAGGACACGGCCGTGTATTACTGTGTGAGA

CACGGGAATTTCGGCAATTCTTATGTCTCGTGGTTCGCTTACTGGGGCCA

AGGGACTCTGGTCACAGTCTCGAGC

The alignment of the murine and humanized sequences of SP34 is indicated below (mSP34VH (SEQ ID NO: 1) and hSP34VH (SEQ ID NO: 6)). CDRs as defined by IMGT nomenclature are underlined. hSP34VH amino acids that are not aligned with mSP34VH are italicized. hSP34VH amino acid sequences that are aligned with mSP34VH are shown as ".".

Similarly, the light chain CDR 1 and 2 of mSP34 were grafted onto the human hIGLV7-46 framework. The amino acid and nucleic acid sequences of the hIGLV7-46 framework are shown below. CDR sequences as defined by IMGT nomenclature are underlined.

hIGLV7-46 Framework
(SEQ ID NO: 51)
QAVVTQEPSLTVSPGGTVTLTCGSS<u>TGAVTSGHY</u>PYWFQQKPGQAPRTLI YD<u>TS</u>NKHSWTPARFSGSLLGGKAALTLSGAQPEDEAEYYC hIGLV7-46 Framework
(SEQ ID NO: 52)
CAGGCTGTGGTGACTCAGGAGCCCTCACTGACTGTGTCCCCAGGAGGGAC

AGTCACTCTCACCTGTGGCTCCAGCACTGGAGCTGTCACCAGTGGTCATT

ATCCCTACTGGTTCCAGCAGAAGCCTGGCCAAGCCCCCAGGACACTGATT

TATGATACAAGCAACAAACACTCCTGGACACCTGCCCGGTTCTCAGGCTC

CCTCCTTGGGGGCAAAGCTGCCCTGACCCTTTCGGGTGCGCAGCCTGAGG

ATGAGGCTGAGTATTACTGC

During DNA synthesis, the CDR3 region of mSP34 was replaced by a non-coding stuffer DNA fragment containing type IIs restriction enzyme to generate an acceptor framework allowing for the insertion of diversified sequences encoding CDR3 regions and effective generation of phage display antibody library following the method described in EP2432878. The humanized VH and acceptor VL were first cloned as a scFv into the pNDS phagemid vector (Ravn et al., 2009, NAR). 3 types of DNA fragments partially randomizing the original CDRL3 of mSP34 were synthesized using a degenerate NNS codon strategy. Each fragment (Fgt a,b,c) diversified 3 consecutive codons of the CDR as indicated below.

(SEQ ID NO 6)

mSP34VH  EVQLVESGGGLVQPKGSLKLSCAAS......MNWVRQAPGKGLEWVAR........Y hSP34VH  ..................................................

mSP34VH  YADSVKDRFTISRDDSQSLLYLQMNNLKTEDTAMYYC...........WGQGTLVTVSS hSP34VH  ..................................................

| CDRL3 | |
|---|---|
| mSP34 | AL WYSNLW V (SEQ ID NO: 7) |
| Fgt a | AL XXXNLW V (SEQ ID NO: 8) |
| Fgt b | AL WYXXXW V SEQ ID NO: 9) |
| Fgt c | AL WYSXXX V SEQ ID NO: 10) |

X = NNS codon

The amino acid and nucleic acid sequences of humanized SP34 variable light chains are shown below. CDR sequences as defined by IMGT nomenclature are underlined.

L3sp34-G1-1-R2-P1_B6 variable light chain
(SEQ ID NO: 29)
QTVVTQEPSLTVSPGGTVTLTCRSS<u>TGAVTTSNY</u>ANWFQQKPGQAPRGLI
G<u>GTN</u>KRAPGTPARFSGSLLGGKAALTLSGAQPEDEAEYYC<u>ALWYANRWV</u>F
GGGTKLTVL

TABLE 3

CDR sequences of selected humanized CD3E scFv binders isolated in Example 2.

| Clone | CDRL1 | CDRL2 | CDRL3 |
|---|---|---|---|
| L3sp34-G1-1-R2-P1_B6 | TGAVTTSNY<br>SEQ ID NO: 11 | GTN<br>SEQ ID NO: 12 | ALWYANRWV<br>SEQ ID NO: 13 |
| L3sp34-G1-2-R2-P1_A10 | TGAVTTSNY<br>SEQ ID NO: 11 | GTN<br>SEQ ID NO: 12 | ALWYKGYWV<br>SEQ ID NO: 14 |
| L3sp34-G1-1-R2-P1_D8 | TGAVTTSNY<br>SEQ ID NO: 11 | GTN<br>SEQ ID NO: 12 | ALWYDGTWV<br>SEQ ID NO: 15 |
| L3sp34-G1-2-R2-P1_F8 | TGAVTTSNY<br>SEQ ID NO: 11 | GTN<br>SEQ ID NO: 12 | ALWYDGKWV<br>SEQ ID NO: 16 |
| L3sp34-G1-1-R2-P1_A11 | TGAVTTSNY<br>SEQ ID NO: 11 | GTN<br>SEQ ID NO: 12 | ALWYDGWWV<br>SEQ ID NO: 17 |
| L3sp34-G1-2-R2-P1_A4 | TGAVTTSNY<br>SEQ ID NO: 11 | GTN<br>SEQ ID NO: 12 | ALWYKQRWV<br>SEQ ID NO: 18 |
| L3sp34-G1-2.4-R2-P1-H4 | TGAVTTSNY<br>SEQ ID NO: 11 | GTN<br>SEQ ID NO: 12 | ALWYNQHWV<br>SEQ ID NO: 19 |
| L3sp34-G1-1-R2-P1_B6 | ACTGGAGCTGTCACCAC<br>TAGCAATTAT<br>SEQ ID NO: 20 | GGTACAAAC<br>SEQ ID NO: 21 | GCACTGTGGTATGCCAA<br>CCGCTGGGTG<br>SEQ ID NO: 22 |
| L3sp34-G1-2-R2-P1_A10 | ACTGGAGCTGTCACCAC<br>TAGCAATTAT<br>SEQ ID NO: 20 | GGTACAAAC<br>SEQ ID NO: 21 | GCACTGTGGTATAAGGG<br>GTACTGGGTG<br>SEQ ID NO: 23 |
| L3sp34-G1-1-R2-P1_D8 | ACTGGAGCTGTCACCAC<br>TAGCAATTAT<br>SEQ ID NO: 20 | GGTACAAAC<br>SEQ ID NO: 21 | GCACTGTGGTATGACGG<br>GACCTGGGTG<br>SEQ ID NO: 24 |
| L3sp34-G1-2-R2-P1_F8 | ACTGGAGCTGTCACCAC<br>TAGCAATTAT<br>SEQ ID NO: 20 | GGTACAAAC<br>SEQ ID NO: 21 | GCACTGTGGTATGACGG<br>CAAGTGGGTG<br>SEQ ID NO: 25 |
| L3sp34-G1-1-R2-P1_A11 | ACTGGAGCTGTCACCAC<br>TAGCAATTAT<br>SEQ ID NO: 20 | GGTACAAAC<br>SEQ ID NO: 21 | GCACTGTGGTATGACGG<br>CTGGTGGGTG<br>SEQ ID NO: 26 |
| L3sp34-G1-2-R2-P1_A4 | ACTGGAGCTGTCACCAC<br>TAGCAATTAT<br>SEQ ID NO: 20 | GGTACAAAC<br>SEQ ID NO: 21 | GCACTGTGGTATAAGCA<br>GAGGTGGGTG<br>SEQ ID NO: 27 |
| L3sp34-G1-24-R2-P1-H4 | ACTGGAGCTGTCACCAC<br>TAGCAATTAT<br>SEQ ID NO: 20 | GGTACAAAC<br>SEQ ID NO: 21 | GCACTGTGGTATAACCA<br>GCACTGGGTG<br>SEQ ID NO: 28 |

-continued
(SEQ ID NO: 30)
CAGACTGTGGTGACCCAGGAGCCCTCACTGACTGTGTCCCCAGGAGGGAC

AGTCACTCTGACCTGTCGCTCCAGCACTGGAGCTGTCACCACTAGCAATT

ATGCCAACTGGTTCCAGCAGAAGCCTGGCCAAGCCCCCCGGGGACTGATT

GGTGGTACAAACAAAAGAGCCCCCGGGACACCTGCCCGGTTCTCAGGCTC

CCTGCTTGGGGGCAAAGCTGCCCTGACCCTTTCGGGTGCGCAGCCTGAGG

ATGAGGCTGAGTATTACTGCGCACTGTGGTATGCCAACCGCTGGGTGTTC

GGCGGAGGGACCAAGCTGACCGTCCTA

L3sp34-G1-2-R2-P1_A10 variable light chain
(SEQ ID NO: 31)
QTVVTQEPSLTVSPGGTVTLTCRSSTGAVTTSNYANWFQQKPGQAPRGLI

GGTNKRAPGTPARFSGSLLGGKAALTLSGAQPEDEAEYYCALWYKGYWVF

GGGTKLTVL (SEQ ID NO: 32)
CAGACTGTGGTGACCCAGGAGCCCTCACTGACTGTGTCCCCAGGAGGGAC

AGTCACTCTGACCTGTCGCTCCAGCACTGGAGCTGTCACCACTAGCAATT

ATGCCAACTGGTTCCAGCAGAAGCCTGGCCAAGCCCCCCGGGGACTGATT

GGTGGTACAAACAAAAGAGCCCCCGGGACACCTGCCCGGTTCTCAGGCTC

CCTGCTTGGGGGCAAAGCTGCCCTGACCCTTTCGGGTGCGCAGCCTGAGG

ATGAGGCTGAGTATTACTGCGCACTGTGGTATAAGGGGTACTGGGTGTTC

GGCGGAGGGACCAAGCTGACCGTCCTA

L3sp34-G1-1-R2-P1_D8 variable light chain
(SEQ ID NO: 33)
QTVVTQEPSLTVSPGGTVTLTCRSSTGAVTTSNYANWFQQKPGQAPRGLI

GGTNKRAPGTPARFSGSLLGGKAALTLSGAQPEDEAEYYCALWYDGTWVF

GGGTKLTVL (SEQ ID NO: 34)
CAGACTGTGGTGACCCAGGAGCCCTCACTGACTGTGTCCCCAGGAGGGAC

AGTCACTCTGACCTGTCGCTCCAGCACTGGAGCTGTCACCACTAGCAATT

ATGCCAACTGGTTCCAGCAGAAGCCTGGCCAAGCCCCCCGGGGACTGATT

GGTGGTACAAACAAAAGAGCCCCCGGGACACCTGCCCGGTTCTCAGGCTC

CCTGCTTGGGGGCAAAGCTGCCCTGACCCTTTCGGGTGCGCAGCCTGAGG

ATGAGGCTGAGTATTACTGCGCACTGTGGTATGACGGGACCTGGGTGTTC

GGCGGAGGGACCAAGCTGACCGTCCTA

L3sp34-G1-2-R2-P1_F8 variable light chain
(SEQ ID NO: 35)
QTVVTQEPSLTVSPGGTVTLTCRSSTGAVTTSNYANWFQQKPGQAPRGLI

GGTNKRAPGTPARFSGSLLGGKAALTLSGAQPEDEAEYYCALWYDGKWVF

GGGTKLTVL (SEQ ID NO: 36)
CAGACTGTGGTGACCCAGGAGCCCTCACTGACTGTGTCCCCAGGAGGGAC

AGTCACTCTGACCTGTCGCTCCAGCACTGGAGCTGTCACCACTAGCAATT

ATGCCAACTGGTTCCAGCAGAAGCCTGGCCAAGCCCCCCGGGGACTGATT

GGTGGTACAAACAAAAGAGCCCCCGGGACACCTGCCCGGTTCTCAGGCTC

CCTGCTTGGGGGCAAAGCTGCCCTGACCCTTTCGGGTGCGCAGCCTGAGG

ATGAGGCTGAGTATTACTGCGCACTGTGGTATGACGGCAAGTGGGTGTTC

GGCGGAGGGACCAAGCTGACCGTCCTA

L3sp34-G1-1-R2-P1_A11 variable light chain
(SEQ ID NO: 37)
QTVVTQEPSLTVSPGGTVTLTCRSSTGAVTTSNYANWFQQKPGQAPRGLI

GGTNKRAPGTPARFSGSLLGGKAALTLSGAQPEDEAEYYCALWYDGWWVF

GGGTKLTVL (SEQ ID NO: 38)
CAGACTGTGGTGACCCAGGAGCCCTCACTGACTGTGTCCCCAGGAGGGAC

AGTCACTCTGACCTGTCGCTCCAGCACTGGAGCTGTCACCACTAGCAATT

ATGCCAACTGGTTCCAGCAGAAGCCTGGCCAAGCCCCCCGGGGACTGATT

GGTGGTACAAACAAAAGAGCCCCCGGGACACCTGCCCGGTTCTCAGGCTC

CCTGCTTGGGGGCAAAGCTGCCCTGACCCTTTCGGGTGCGCAGCCTGAGG

ATGAGGCTGAGTATTACTGCGCACTGTGGTATGACGGCTGGTGGGTGTTC

GGCGGAGGGACCAAGCTGACCGTCCTA

L3sp34-G1-2-R2-P1_A4 variable light chain
(SEQ ID NO: 39)
QTVVTQEPSLTVSPGGTVTLTCRSSTGAVTTSNYANWFQQKPGQAPRGLI

GGTNKRAPGTPARFSGSLLGGKAALTLSGAQPEDEAEYYCALWYKQRWVF

GGGTKLTVL (SEQ ID NO: 40)
CAGACTGTGGTGACCCAGGAGCCCTCACTGACTGTGTCCCCAGGAGGGAC

AGTCACTCTGACCTGTCGCTCCAGCACTGGAGCTGTCACCACTAGCAATT

ATGCCAACTGGTTCCAGCAGAAGCCTGGCCAAGCCCCCCGGGGACTGATT

GGTGGTACAAACAAAAGAGCCCCCGGGACACCTGCCCGGTTCTCAGGCTC

CCTGCTTGGGGGCAAAGCTGCCCTGACCCTTTCGGGTGCGCAGCCTGAGG

ATGAGGCTGAGTATTACTGCGCACTGTGGTATAAGCAGAGGTGGGTGTTC

GGCGGAGGGACCAAGCTGACCGTCCTA

L3sp34-G1-2.4-R2-P1_114 variable light chain
(SEQ ID NO: 41)
QTVVTQEPSLTVSPGGTVTLTCRSSTGAVTTSNYANWFQQKPGQAPRGLI

GGTNKRAPGTPARFSGSLLGGKAALTLSGAQPEDEAEYYCALWYNQHWVF

GGGTKLTVL (SEQ ID NO: 42)
CAGACTGTGGTGACCCAGGAGCCCTCACTGACTGTGTCCCCAGGAGGGAC

AGTCACTCTGACCTGTCGCTCCAGCACTGGAGCTGTCACCACTAGCAATT

ATGCCAACTGGTTCCAGCAGAAGCCTGGCCAAGCCCCCCGGGGACTGATT

GGTGGTACAAACAAAAGAGCCCCCGGGACACCTGCCCGGTTCTCAGGCTC

CCTGCTTGGGGGCAAAGCTGCCCTGACCCTTTCGGGTGCGCAGCCTGAGG

ATGAGGCTGAGTATTACTGCGCACTGTGGTATAACCAGCACTGGGTGTTC

GGCGGAGGGACCAAGCTGACCGTCCTA

Example 3: Characterization of Humanized Variants of Murine SP34

Selected scFv candidates were reformatted into human IgG1 format for further characterization.

The purified IgGs were tested for binding to human and cynomolgus recombinant CD3ε protein as well as irrelevant proteins. As controls, were used SP34 as well as an I2C anti-CD3ε antibody generated using the sequence described in the patent application WO2011121110. The dose-response experiments indicated that all these antibodies showed comparable specific binding to both cynomolgus and human CD3ε proteins FIG. 1.

Figure 3:
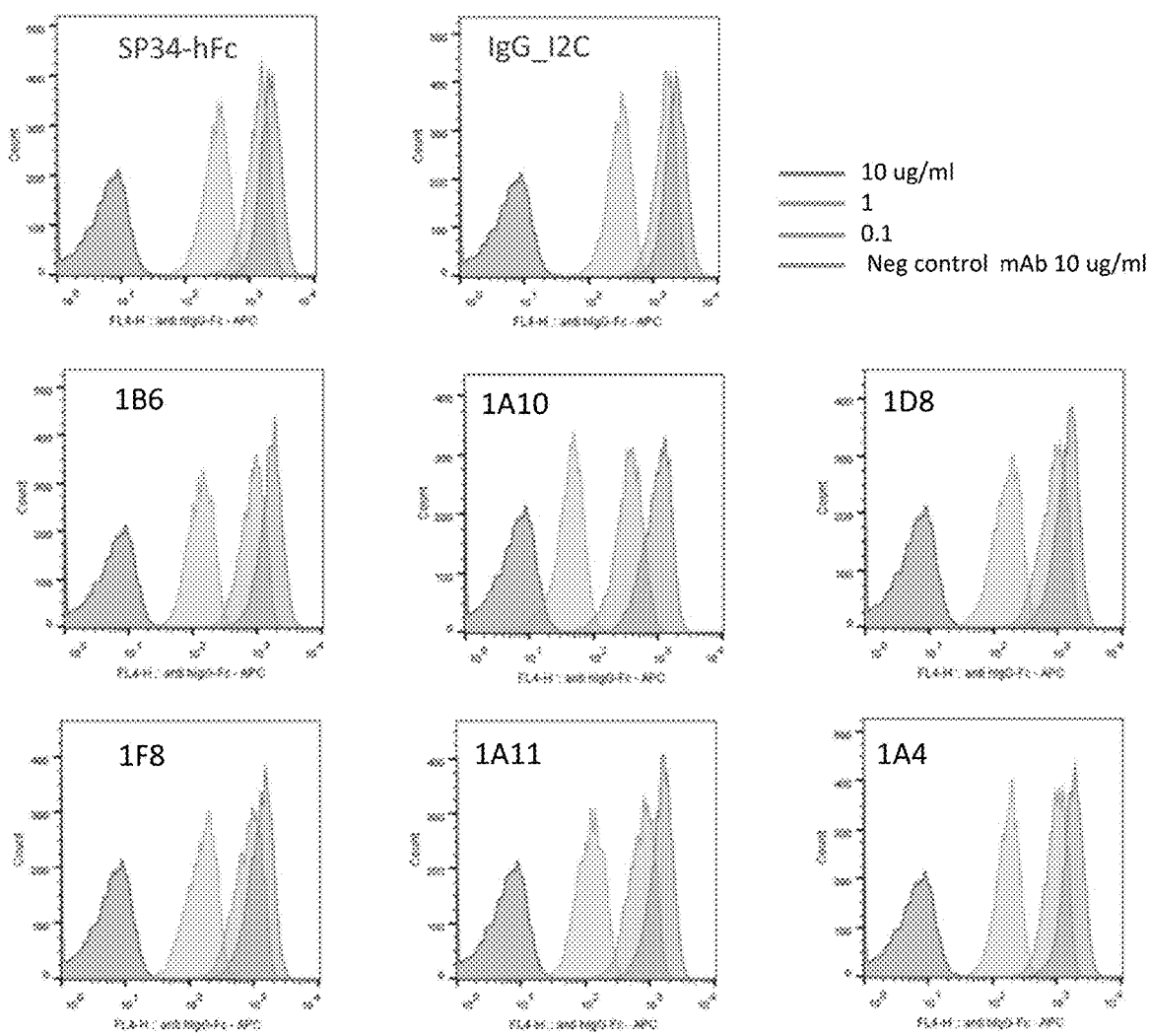
FIG. 3 Graphs showing the binding signals using FACS and obtained with control and candidate anti-CD3ε antibodies for staining of CD4+ T cell population isolated from healthy human donors.
Figure 4:
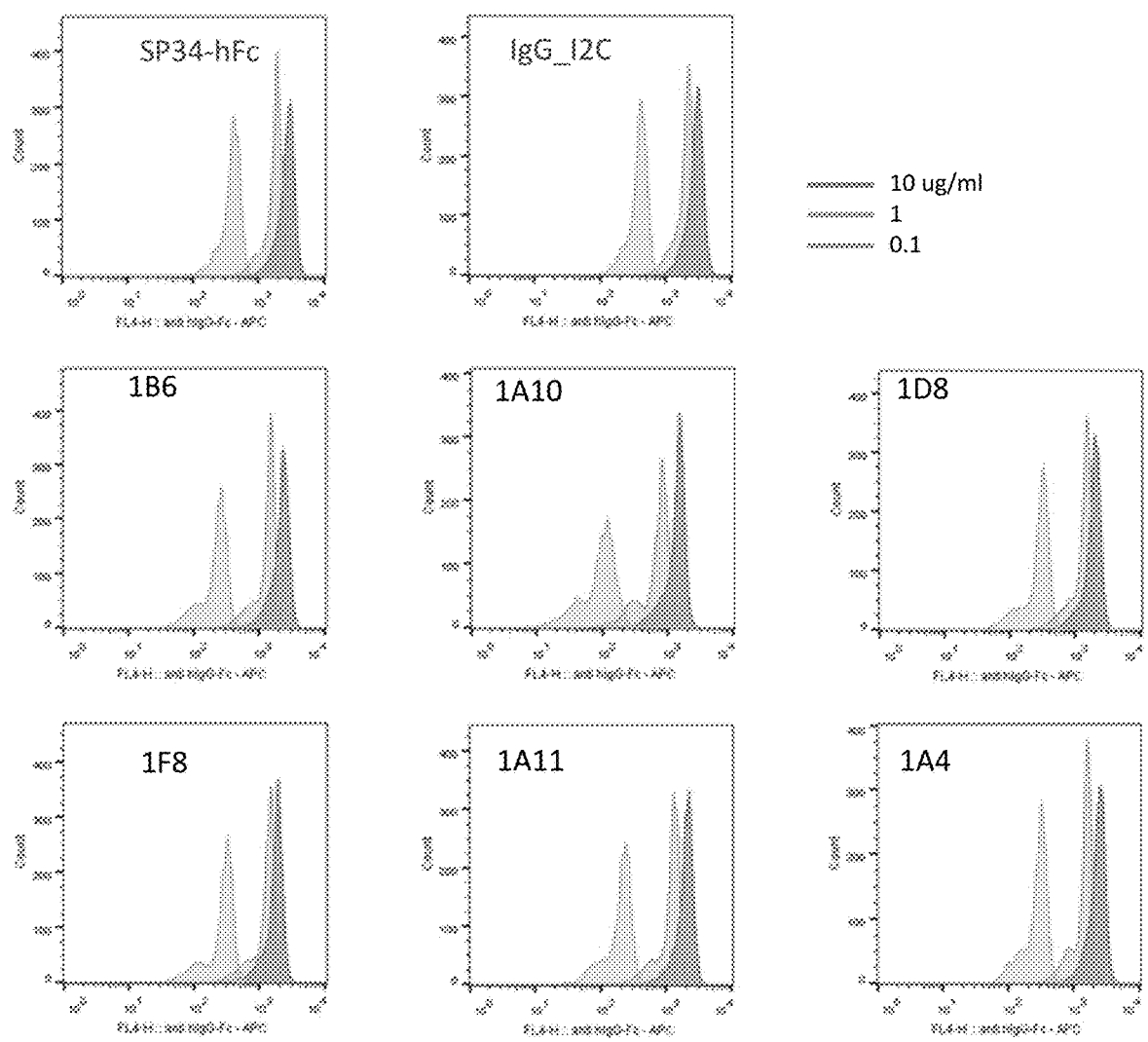
FIG. 4 Graphs showing the binding signals using FACS and obtained with control and candidate anti-CD3ε antibodies for staining of CD8+ T cell population isolated from healthy human donors.
Figure 5:
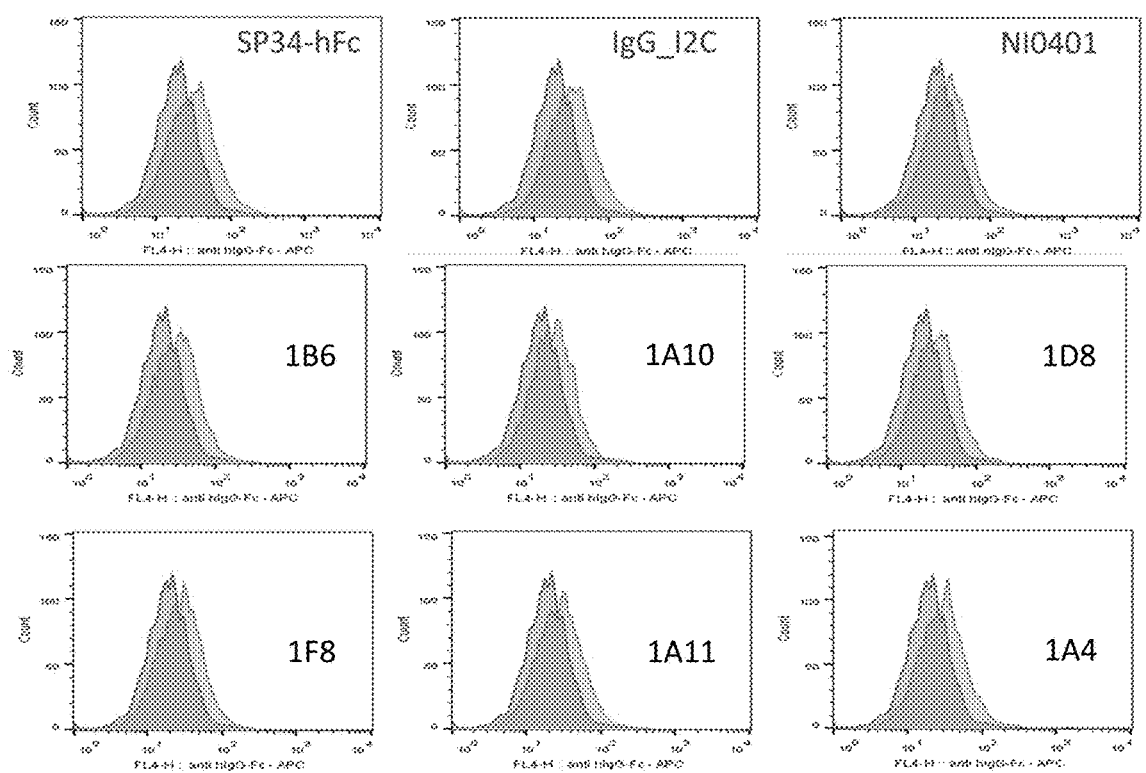
FIG. 5 Graphs showing the binding signals using FACS and obtained with control and candidate anti-CD3ε antibodies for staining of CD20+ B cell population isolated from healthy human donors.

Binding was also evaluated by FACS on different cell populations including T cell lines and natural cell populations derived from healthy blood donors. First, control and antiCD3ε candidates were tested at different concentration on the human T cell line Jurkat. The results shown in FIG. 3 show that the different candidates bind to Jurkat in a dose dependent manner. The same experiments were performed against the CD3ε deficient T cell line and no binding was observed. Binding to native cell populations was performed by isolating PBMCs from healthy donors and evaluating binding to CD4+ and CD8+ T cells as well as B cells. A dose dependent increase in fluorescent staining was observed for both CD4+ and CD8+ populations (FIGS. 4 and 5), while no staining was observed on B cells at the highest concentration of 10 µg/ml. The florescent intensities obtained at different concentrations varied between candidates suggesting difference in binding affinities. The mean fluorescence values for the different candidates at a non-saturating antibody concentration are listed in Table 4.

TABLE 4

Mean fluorescence intensities measured using and antibody concentration of 0.1 µg/ml.

| Antibody | MFI on CD4+ T cells | MFI on CD8+ T cells |
|---|---|---|
| IgG 1B6 | 231 | 130 |
| IgG 1A10 | 96 | 43 |
| IgG 1D8 | 286 | 161 |
| IgG 1F8 | 284 | 157 |
| IgG 1A11 | 205 | 119 |
| IgG 1A4 | 284 | 173 |

These values suggest that IgG 1D8, 1F8 and 1A4 have the highest binding capacity, while IgG 1B6 and 1A11 have an intermediate binding capacity and IgG 1A10 displays the lowest binding capacity. Having a panel of anti-CD3ε antibodies showing different apparent affinities is of interest as it can have functional consequence when constructing T cell redirecting bispecific antibodies.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody that specifically binds CD3ε comprising a heavy chain variable region comprising:
   a) a variable heavy chain complementarity determining region 1 (CDRH1) comprising the amino acid sequence of GFTFNTYA (SEQ ID NO: 3);
   b) a variable heavy chain complementarity determining region 2 (CDRH2) comprising the amino acid sequence of IRSKYNNYAT (SEQ ID NO: 4); and
   c) variable heavy chain complementarity determining region 3 (CDRH3) comprising the amino acid sequence of VRHGNFGNSYVSWFAY (SEQ ID NO: 5); and
   a light chain variable region comprising:
   d) a variable light chain complementarity determining region 1 (CDRL1) comprising the amino acid sequence of TGAVTTSNY (SEQ ID NO: 11);
   e) a variable light chain complementarity determining region 2 (CDRL2) comprising the amino acid sequence of GTN (SEQ ID NO: 12); and
   f) a variable light chain complementarity determining region 3 (CDRL3) comprising the amino acid sequence selected from the group consisting of ALWYANRWV (SEQ ID NO: 13), ALWYKGYWV (SEQ ID NO: 14), ALWYDGTWV (SEQ ID NO: 15), ALWYDGKWV (SEQ ID NO: 16), ALWYDGWWV (SEQ ID NO: 17), ALWYKQRWV (SEQ ID NO: 18) and ALWYNQHWV (SEQ ID NO: 19).

2. The antibody of claim 1, wherein the variable heavy chain region comprises a hIGHV3-73 framework region.

3. The antibody of claim 1, wherein the variable light chain region comprises a hIGLV7-46 framework region.

4. The antibody of claim 1, wherein the heavy chain variable region comprises an amino acid sequence of SEQ ID NO: 6 and the light chain variable region comprises an amino acid sequence of SEQ ID NO: 29, 31, 33, 35, 37, 39 or 41.

5. The antibody of claim 4, wherein the heavy chain variable region comprises an amino acid sequence of SEQ ID NO: 6 and the light chain variable region comprises an amino acid sequence of SEQ ID NO: 39.

6. The antibody of claim 1, wherein the CD3ε is human CD3ε or cynomolgus monkey CD3ε.

7. The antibody of claim 1, wherein the antibody is an antigen binding fragment thereof, and wherein the antigen binding fragment is a single chain antibody (scAb), a Fab, a Fab', a F(ab)2, a F(ab')₂, a single chain variable fragment (scFv), a Fv, or a scFv-Fc fragment.

8. The antibody of claim 1, wherein the antibody is a chimeric antibody or a humanized antibody.

9. The antibody of claim 1, wherein the antibody is an IgG isotype.

10. The antibody of claim 1, wherein the antibody is an IgG1 isotype.

11. The antibody of claim 1, wherein the antibody comprises two copies of a single heavy chain polypeptide and a first light chain and a second light chain, wherein the first and the second light chains are different.

12. The antibody of claim 11, wherein at least a portion of the first light chain is of the Kappa type and at least a portion of the second light chain is of the Lambda type.

13. The antibody of claim 12, wherein the first light chain comprises at least a Kappa constant region.

14. The antibody of claim 13, wherein the second light chain comprises at least a Lambda constant region.

15. The antibody of claim 14, wherein the second light chain further comprises a Lambda variable region.

16. The antibody of claim 14, wherein the second light chain further comprises a Kappa variable region.

17. The antibody of claim 11, wherein the first light chain comprises a Kappa constant region and a Kappa variable region, and wherein the second light chain comprises a Lambda constant region and a Lambda variable region.

18. A pharmaceutical composition comprising the antibody of claim 1.

19. A method of treating and/or delaying the progression of a cancer, comprising administering to a subject in need thereof the pharmaceutical composition of claim 18.

20. The method of claim 19, wherein the cancer is leukemia, lymphoma, breast cancer, colon cancer, ovarian cancer, bladder cancer, prostate cancer, glioma, lung cancer, bronchial cancer, colorectal cancer, pancreatic cancer, esophageal cancer, liver cancer, urinary cancer, kidney cancer, pelvis cancer, oral cavity cancer, pharynx cancer, uterine corpus cancer, or melanoma.

21. A method of T-cell retargeting comprising administering to a subject in need thereof the pharmaceutical composition of claim 18.

22. The antibody of claim 1, wherein
i) the CDRH1 comprises the amino acid sequence of SEQ ID NO: 3; the CDRH2 comprises the amino acid sequence of SEQ ID NO: 4; the CDRH3 comprises the amino acid sequence of SEQ ID NO: 5; the CDRL1 comprises the amino acid sequence of SEQ ID NO: 11; the CDRL2 comprises the amino acid sequence of SEQ ID NO: 12; and the CDRL3 comprises the amino acid sequence of SEQ ID NO: 18;
ii) the CDRH1 comprises the amino acid sequence of SEQ ID NO: 3; the CDRH2 comprises the amino acid sequence of SEQ ID NO: 4; the CDRH3 comprises the amino acid sequence of SEQ ID NO: 5; the CDRL1 comprises the amino acid sequence of SEQ ID NO: 11; the CDRL2 comprises the amino acid sequence of SEQ ID NO: 12; and the CDRL3 comprises the amino acid sequence of SEQ ID NO: 13;
iii) the CDRH1 comprises the amino acid sequence of SEQ ID NO: 3; the CDRH2 comprises the amino acid sequence of SEQ ID NO: 4; the CDRH3 comprises the amino acid sequence of SEQ ID NO: 5; the CDRL1 comprises the amino acid sequence of SEQ ID NO: 11; the CDRL2 comprises the amino acid sequence of SEQ ID NO: 12; and the CDRL3 comprises the amino acid sequence of SEQ ID NO: 14;
iv) the CDRH1 comprises the amino acid sequence of SEQ ID NO: 3; the CDRH2 comprises the amino acid sequence of SEQ ID NO: 4; the CDRH3 comprises the amino acid sequence of SEQ ID NO: 5; the CDRL1 comprises the amino acid sequence of SEQ ID NO: 11; the CDRL2 comprises the amino acid sequence of SEQ ID NO: 12; and the CDRL3 comprises the amino acid sequence of SEQ ID NO: 15;
v) the CDRH1 comprises the amino acid sequence of SEQ ID NO: 3; the CDRH2 comprises the amino acid sequence of SEQ ID NO: 4; the CDRH3 comprises the amino acid sequence of SEQ ID NO: 5; the CDRL1 comprises the amino acid sequence of SEQ ID NO: 11; the CDRL2 comprises the amino acid sequence of SEQ ID NO: 12; and the CDRL3 comprises the amino acid sequence of SEQ ID NO: 16;
vi) the CDRH1 comprises the amino acid sequence of SEQ ID NO: 3; the CDRH2 comprises the amino acid sequence of SEQ ID NO: 4; the CDRH3 comprises the amino acid sequence of SEQ ID NO: 5; the CDRL1 comprises the amino acid sequence of SEQ ID NO: 11; the CDRL2 comprises the amino acid sequence of SEQ ID NO: 12; and the CDRL3 comprises the amino acid sequence of SEQ ID NO: 17; or
vii) the CDRH1 comprises the amino acid sequence of SEQ ID NO: 3; the CDRH2 comprises the amino acid sequence of SEQ ID NO: 4; the CDRH3 comprises the amino acid sequence of SEQ ID NO: 5; the CDRL1 comprises the amino acid sequence of SEQ ID NO: 11; the CDRL2 comprises the amino acid sequence of SEQ ID NO: 12; and the CDRL3 comprises the amino acid sequence of SEQ ID NO: 19.

23. The antibody of claim 22, wherein the CDRH1 comprises the amino acid sequence of SEQ ID NO: 3; the CDRH2 comprises the amino acid sequence of SEQ ID NO: 4; the CDRH3 comprises the amino acid sequence of SEQ ID NO: 5; the CDRL1 comprises the amino acid sequence of SEQ ID NO: 11; the CDRL2 comprises the amino acid sequence of SEQ ID NO: 12;
and the CDRL3 comprises the amino acid sequence of SEQ ID NO: 18.

24. The antibody of claim 1, wherein the antibody is a monoclonal antibody.

* * * * *

UNITED STATES PATENT AND TRADEMARK OFFICE
CERTIFICATE OF CORRECTION

PATENT NO. : 11,203,646 B2
APPLICATION NO. : 16/353916
DATED : December 21, 2021
INVENTOR(S) : Fischer et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 180 days.

Signed and Sealed this
Thirteenth Day of December, 2022

Katherine Kelly Vidal
*Director of the United States Patent and Trademark Office*